Figure 1A:
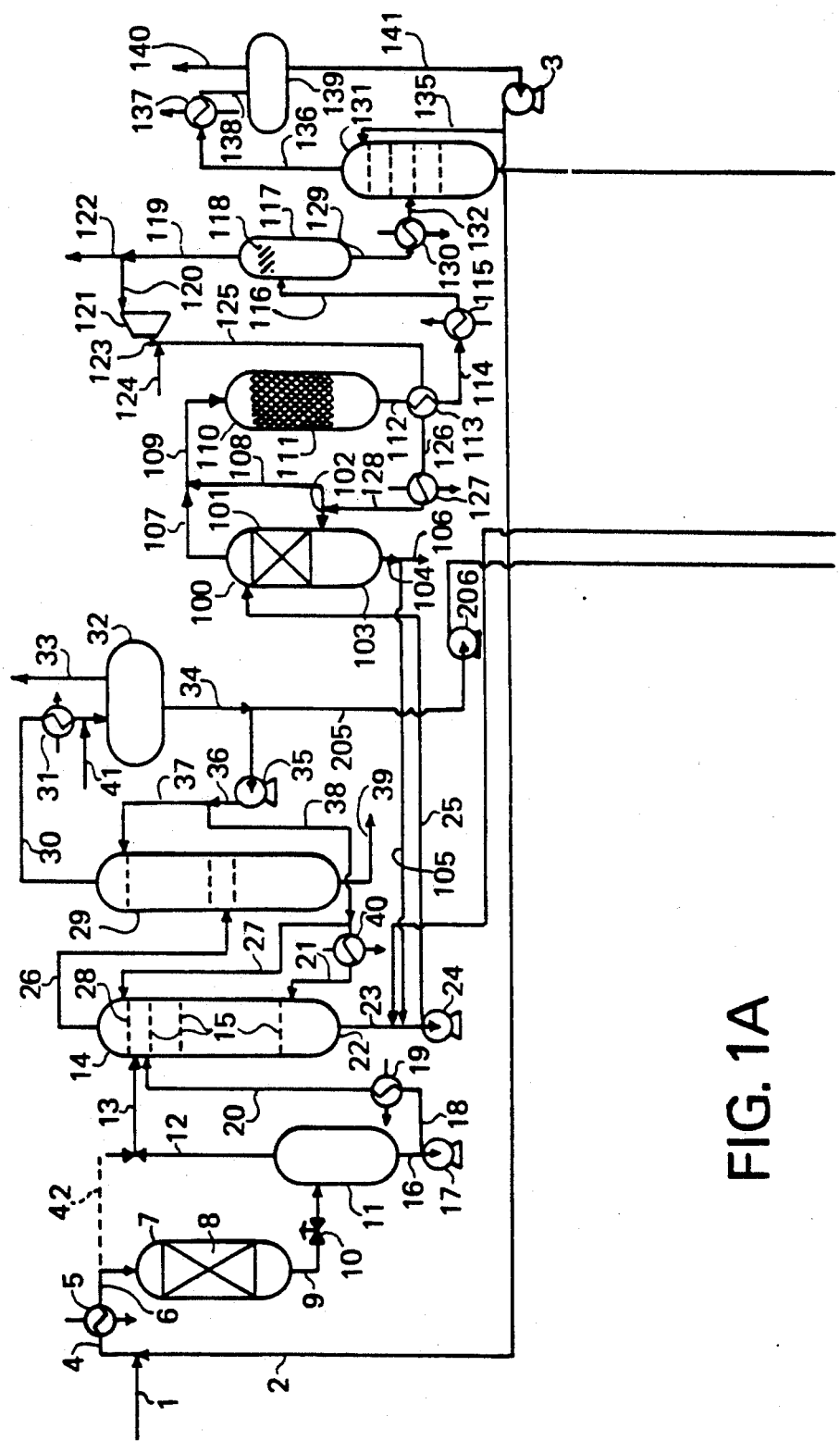

United States Patent [19]

Wilmott et al.

[11] Patent Number: 5,157,168
[45] Date of Patent: Oct. 20, 1992

[54] PROCESS FOR THE PRODUCTION OF FATTY ALCOHOLS

[75] Inventors: Martyn Wilmott, Norton, Stockton-on-Tees; George E. Harrison, Billericay; John Scarlett, Spennymoor; Michael A. Wood, Middlesbrough; Donald H. McKinley, Radlett, all of England

[73] Assignee: Davy McKee (London) Limited, London, England

[21] Appl. No.: 721,438

[22] PCT Filed: Jan. 16, 1990

[86] PCT No.: PCT/GB90/00063
§ 371 Date: Aug. 12, 1991
§ 102(e) Date: Aug. 12, 1991

[87] PCT Pub. No.: WO90/08121
PCT Pub. Date: Jul. 26, 1990

[30] Foreign Application Priority Data

Jan. 17, 1989 [GB] United Kingdom ............... 8900997
Dec. 18, 1989 [GB] United Kingdom ............... 8928540

[51] Int. Cl.$^5$ ............... C07C 27/02; C07C 31/125; C07C 29/149
[52] U.S. Cl. ............... 568/877; 568/885
[58] Field of Search ............... 568/877, 885

[56] References Cited

U.S. PATENT DOCUMENTS

| | | | |
|---|---|---|---|
| 1,491,076 | 4/1924 | Burghart | 568/877 |
| 3,173,959 | 3/1965 | Rittmeister | 568/885 |
| 3,949,007 | 4/1976 | Grolig et al. | 568/877 |

FOREIGN PATENT DOCUMENTS

| | | | |
|---|---|---|---|
| 188334 | 9/1985 | Japan | 568/877 |
| 7103178 | 9/1971 | Netherlands | 508/877 |
| 734182 | 5/1980 | U.S.S.R. | 568/877 |
| 795573 | 5/1958 | United Kingdom | 568/877 |

*Primary Examiner*—J. E. Evans
*Attorney, Agent, or Firm*—Rothwell, Figg, Ernst & Kurz

[57] ABSTRACT

An improved process for the production of fatty alcohols is provided. The fatty alcohols are produced by hydrogenation of lower alkyl esters, especially methyl esters, of fatty acids derived from natural triglycerides, under conditions which minimize formation of by-product alkanes and ethers. The hydrogenation is followed by refining of any resulting ester-containing hydrogenation product to produce a substantially ester free fatty alcohol.

17 Claims, 9 Drawing Sheets

PROCESS FOR THE PRODUCTION OF FATTY ALCOHOLS

This invention relates to a process for the production of fatty alcohols.

Fatty alcohols, or higher alcohols as they are sometimes designated, are monohydric aliphatic alcohols containing six or more carbon atoms which are derived either from natural sources or are synthesised from petroleum feedstocks. They are often classified by their market usage. As the primary end use of primary alcohols containing between about 6 and about 11 carbon atoms is the production of plasticiser esters, such alcohols are often termed plasticiser alcohols. For higher alcohols containing, for example, from about 11 up to about 20 carbon atoms, the major use is for the production of synthetic detergents; hence such alcohols are often termed detergent alcohols. The distinction between plasticiser alcohols and detergent alcohols is somewhat arbitrary and there is some production of phthalate esters from a $C_{13}$ "oxo" alcohol and also some production of, for example, nonionic surfactants from $C_8$ to $C_{10}$ alcohols.

Although there are some natural products which contain esters which can be hydrogenated to produce alcohols in the plasticiser range, these are more usually produced synthetically from petroleum feedstocks by, for example, the so-called "oxo" process, a process which is also termed oxonation or hydroformylation. Detergent range alcohols, on the other hand, are typically produced by hydrogenation of lower molecular alkyl esters of fatty acids. Such esters can be produced by transesterification of natural triglycerides or by esterification of the fatty acids obtained by hydrolysis of such triglycerides. Examples of triglycerides which can be used as raw materials include natural oils, such as coconut oil, rape seed oil, and palm oils, and animal fats, such as lard, tallow, and fish oil. As such natural raw materials usually contain mixtures of triglycerides, the alcohol products obtained upon hydrogenation are also mixtures of n-alkanols of differing molecular weight Such mixtures of alkanols are acceptable for production of detergents without prior separation of the alkanols one from another.

Whatever the commercial end use of the fatty alcohol or fatty alcohol mixture the user generally insists that the alcohol product must have as low an acid value as possible and also as low a saponification value as possible. The acid value (AV) is a measure of the free acid content of the alcohol product and is defined as the number of mg of KOH required to neutralise the free fatty acid in 1 g of alcohol. The saponification value (SV) gives, together with the acid value, a measure of the free ester content of the alcohol product and is defined as the number of mg of KOH required to saponify the esters and acids in 1 g of alcohol. The ester value (EV) is the number obtained by subtracting the acid value from the saponification value (EV=SV−AV). In all cases the lower the value is (AV, SV, or EV), the better is considered to be the quality of the alcohol product. Another measure of purity of saturated alcohols is the iodine value (IV), i.e. the number of g of $I_2$ absorbed by 100 g of the alcohol The iodine value indicates the ethylenic double bond content of the alcohol product. Again, it is generally considered desirable to have as low an iodine value as possible for a saturated alcohol.

Examples of commercial fatty alcohol products are the products sold under the following trade names:

| Descriptive Name | Trade Mark | Derived from | Approx. composition, wt %, 100% alcohol basis | | | | |
|---|---|---|---|---|---|---|---|
| | | | $C_{12}$ | $C_{14}$ | $C_{16}$ | $C_{18}$ | $C_{20}$ |
| dodecanol | CO-1214 | coconut | 67 | 26 | 7 | | |
| | Dehydag | coconut | 72 | 27 | 1 | | |
| tetradecanol-octadecanol | CO-1418 | coconut | 12 | 43 | 22 | 23 | |
| hexadecenol | CO-1695 | coconut | | 1 | 96 | 3 | |
| hexadecanol-octadecanol | TA-1618 | tallow | | 4 | 28 | $67^a$ | 1 |
| octadecenol | CO-1895 | coconut | | | 2 | 97 | 1 |
| octadecenol | Dehydag HD | natural oils | | | 4 | $94^b$ | 2 |
| octadecenol-octadecanol | Dehydag 60/65 | natural oils | 1 | 4 | 26 | $68^b$ | 1 |

Notes:
$a$ = includes 1% $C_{17}$ alcohol
$b$ = octadecenol

The esters usually used as raw materials for the production of detergent range alcohols are the methyl esters. A problem arises in refining of the product alcohol mixtures because the boiling point of one or more of the methyl esters present in the ester mixture which is hydrogenated will usually be close to that of one of the product alcohols. Hence it becomes difficult, if not impossible, to separate by distillation any unconverted methyl esters from the product alcohol mixture.

As an illustration of the difficulty of separating fatty alcohols from methyl fatty acid esters, particularly from mixtures containing a major amount of a mixture of fatty alcohols and a minor amount of a mixture of methyl fatty acid esters, reference may be made to the following list of boiling points:

| Substance | Boiling point | Pressure mm Hg (bar) |
|---|---|---|
| 1-dodecanol | 150° C. | 20 (0.027) |
| methyl laurate | 149° C. | 20 (0.027) |
| 1-tetradecanol | 167° C. | 15 (0.020) |
| methyl myristate | 170° C. | 15 (0.020) |
| 1-hexadecanol | 189.5° C. | 15 (0.020) |
| methyl palmitate | 192° C. | 15 (0.020) |
| 1-octadecanol | 210° C. | 15 (0.020) |
| methyl stearate | 213° C. | 15 (0.020) |

A mixture containing all of these components, such as might be produced by hydrogenation of a mixture of methyl esters of $C_{12}$- to $C_{18}$-fatty acids produced by hydrolysis of a natural triglyceride, is difficult (if not impossible) to separate satisfactorily by distillation without recourse to use of multiple distillation columns.

To avoid the expense of multiple distillation columns, one of two approaches is normally adopted. The first approach involves use of somewhat vigorous hydrogenation conditions, including use of high pressures and temperatures so as to ensure that as small a proportion of unconverted methyl esters remains in the hydrogenation product. Although this largely obviates the problem of separating the methyl esters from the product alcohols, the use of vigorous hydrogenation conditions has drawbacks, particularly in that such conditions also tend to increase the yield of alkane and ether byproducts which represent a significant loss of potentially valuable alcohols. In addition catalyst consumption is rather high and the use of high pressure equipment increases the capital and running costs of the plant.

The second approach to the problems associated with the presence of unconverted esters in the alcohol hydrogenation product is to use less vigorous hydrogenation conditions, which reduces the loss of alcohol product by formation of alkane and ether byproducts, with subsequent removal of the unconverted ester by hydrolysis with hot aqueous alkali, such as hot sodium hydroxide solution. In this case the remaining ester is converted to a fatty acid salt which is lost in the aqueous phase. In addition this procedure involves consumption of sodium hydroxide or other alkali. Finally, as the sodium or other alkali metal salts of the fatty acids act as soaps, problems may arise in separating the aqueous phase from the alcohol product due to formation of emulsions.

In the esterification of fatty acids perhaps the most widely used catalysts are sulphuric acid and organic sulphonic acids, such as p-toluenesulphonic acid. Although these catalysts are efficient, they are homogeneous catalysts and a neutralisation step is necessary before ester purification can be attempted. Typically washing with an alkali, such as sodium hydroxide solution, is used in such a neutralisation step. As esterification is an equilibrium process, a disadvantage of this procedure is that the washing step also results in removal of any unreacted fatty acid in the wash liquor. Normally it is uneconomic to attempt to recover the unreacted acid from its salt in the wash liquor so that this may represent a significant loss of process efficiency. In addition some ester may be lost in this washing step. The losses of ester in the aqueous alkali phase will depend on the solubility of the ester in such solutions. Furthermore the disposal of the wash liquor may present environmental problems which may be aggravated by the presence of the organic carboxylic acid salt in the wash liquor. In addition, particularly when long chain fatty acids are involved, problems may arise in the washing step due to formation of emulsions that are stabilised by the alkali metal fatty acid salts, which are surface active, and that are often difficult to separate into their component aqueous and organic phases. The stability of such emulsions is known to vary in an erratic way, thus making the design of the organic phase/aqueous phase separation equipment difficult. Therefore it is difficult to practise an esterification process with a homogeneous catalyst on a continuous basis. As a result batch processing is usually adopted, a factor which may affect product quality from batch to batch. An additional disadvantage of the use of such homogeneous catalysts as sulphuric acid and p-toluenesulphonic acid is the risk of contamination of the ester with sulphur-containing components. Such sulphur-containing components can interfere seriously with subsequent hydrogenation.

For further background information about the production of fatty alcohols reference may be had to the following reviews:

1. "Fatty alcohols", by J. A. Monick, J. Am. Oil Chemists' Soc., November 1979, Vol. 56, pages 853A to 860A;
2. "Natural fats and oils route to fatty alcohols", by Henning Buchold, Chemical Engineering, Feb. 21, 1985, pages 42 and 43;
3. "Manufacture of Fatty Alcohols Based on Natural Fats and Oils", by Udo R. Kreutzer, JAOCS, Vol. 61, No. 2 (February 1984), pages 343 to 348;
4. "Production of Fatty Alcohols from Fatty Acids", by Theodor Voeste and Henning Buchold, JAOCS, Vol. 61, No. 2 (February 1984), pages 350 to 352;
5. "Alcohols, higher aliphatic", Kirk-Othmer Encyclopedia of Chemical Technology, Third Edition (1978), Vol. 1, (published by J. Wiley & Sons. Inc., New York), pages 716 to 739; and
6. "Technical Processes for the Manufacture of Fatty Alcohols" by H.-D. Kompp and H. P. Kubersky, in "Fatty Alcohols—Raw Materials, Methods, Uses" published in 1982 by Henkel KGaA, Dusseldorf, at pages 49 to 74.

It would be desirable to provide a method enabling substantially ester free fatty alcohols to be produced by hydrogenation of a methyl fatty acid ester feedstock under relatively mild conditions with less formation of byproduct alkane than occurs in conventional methods of manufacture of fatty alcohols by this route, even though the selected hydrogenation conditions result in the presence of significant amounts of unconverted methyl fatty acid ester in the crude hydrogenation product. The provision of such an improved method would result in improved yield of fatty alcohols, since the process losses due to alkane byproduct formation would be reduced.

The present invention accordingly seeks to provide an improved process for production of fatty alcohols by hydrogenation of lower alkyl esters, especially methyl esters, of fatty acids derived from natural triglycerides, under conditions which minimise formation of byproduct alkanes and ethers followed by refining of the resulting ester containing hydrogenation product.

According to the present invention there is provided a process for the production of fatty alcohols in which a fatty acid or fatty acid mixture is esterified in an esterification step with a lower alkanol to form the corresponding lower alkyl fatty acid ester or esters, in which the resulting lower alkyl fatty acid ester or esters is or are subjected to hydrogenation in the presence of a heterogeneous ester hydrogenation catalyst to yield an ester hydrogenation product comprising a fatty alcohol or alcohols, and in which the ester hydrogenation product is subjected to product refining for recovery of fatty alcohol or alcohols therefrom, characterised in that the esterification step includes continuously supplying the fatty acid or fatty acid mixture in liquid phase to an esterification zone maintained under esterification conditions and containing a charge of a solid esterification catalyst containing sulphonic acid groups and/or carboxylic acid groups in countercurrent to a vaporous stream containing vapour of the fatty alkanol, that the esterification zone is supplied with a feed stream of lower alkanol vapour having a water content of less than about 5 mole %, that a vaporous exit stream containing lower alkanol vapour and water of esterification is recovered from the esterification zone, that a lower alkyl fatty acid ester stream is recovered from the esterification zone that contains at least about 99 mole % of lower alkyl fatty acid ester, that lower alkyl fatty acid ester or ester mixture recovered from the esterification step is vaporised in a stream of hydrogen and passed in vapour form through a hydrogenation zone containing a charge of a solid ester hydrogenation catalyst under vapour phase hydrogenation conditions such that the vaporous mixture in contact with the catalyst is always above its dew point, that the resulting hydrogenation product is collected and contains at least about 0.5 mole % of unreacted lower alkyl fatty acid ester in addition to product fatty alcohol or alcohols, that the hydrogenation product is subjected to transesterification in a first transesterification zone maintained under transesterification conditions, thereby to convert unreacted lower alkyl fatty acid ester in the hydrogenation product by reaction with product fatty alcohol or alcohols into a wax ester or wax esters derived from the product alcohol or a product alcohol and from a fatty acid, that unreacted lower alkanol is evaporated from the resulting mixture, and that the now substantially lower alkanol free mixture is further distilled to yield (i) an overhead fraction that contains the product alcohol or alcohols and is substantially free from lower alkyl fatty acid ester and (ii) a distillation residue comprising fatty alcohol or alcohols and wax ester or esters.

In a particularly preferred process the distillation residue (ii) is subjected to transesterification in the presence of added lower alkanol in a second transesterification zone maintained under transesterification conditions, thereby to reconvert wax ester or esters to lower alkyl fatty acid ester or esters and to fatty alcohol or alcohols, followed by evaporation of lower alkanol to yield a liquid residue that is substantially free from lower alkanol and then by distillation of fatty alcohol or alcohols and lower alkyl fatty acid ester or esters present in this liquid residue to produce (a) an overhead product containing a mixture of lower alkyl fatty acid ester or esters and fatty alcohol or alcohols and (b) a relatively involatile residue. This relatively involatile residue contains wax esters and possibly also a transesterification catalyst if one is used in the second transesterification zone.

In this specification all figures in "mole %" are calculated on a lower alkanol free basis, except where the context indicates otherwise. Also the term "fatty alcohol" means a linear alkanol containing from about 6 to about 26 carbon atoms. Preferred fatty alcohols contain from about 10 to about 20 carbon atoms. Typical fatty alcohols include 1-decanol, 1-dodecanol, 1-tetradecanol, 1-hexadecanol, 1-octadecanol, 1-octadecenol and the like, and mixtures thereof. The term "lower alkyl" means $C_1$- to $C_4$-alkyl, including methyl, ethyl, n-propyl, iso-propyl, n-butyl, iso-butyl and sec-butyl. The preferred lower alkyl radical is methyl. Similarly the term "lower alkanol" embraces $C_1$ to $C_4$ alkanols, including methanol, ethanol, n-propanol, iso-propanol, n-butanol, iso-butanol, and sec-butanol. Methanol is the preferred lower alkanol. By the term "fatty acids" we mean linear saturated, unsaturated or polyunsaturated aliphatic acids, such as linear alkyl, alkenyl, or hydroxyalkenyl carboxylic acids containing from about 6 to about 26 carbon atoms, preferably about 10 to about 20 carbon atoms. Examples of such fatty acids are decanoic acid (capric acid), dodecanoic acid (lauric acid), tetradecanoic acid (myristic acid), pentadecanoic acid, hexadecanoic acid (palmitic acid), heptadecanoic acid (margaric acid), octadecanoic acid (stearic acid or isostearic acid), octadecenoic acids (oleic acid, linoleic acid or linolenic acid), hydroxyoctadecenoic acid (ricinoleic acid), eicosanoic acid (arachidic acid) and docosanoic acid (behenic acid). Mixtures of fatty acids are of especial importance as raw materials from which the lower alkyl fatty acid esters used as starting material in the hydrogenation step are prepared. Such mixtures of acids can be obtained by hydrolysis of naturally occurring triglycerides such as coconut oil, rape seed oil, palm oils, tallow, lard and fish oils. If desired, such mixtures of acids can be subjected to distillation to remove lower boiling acids having a lower boiling point than a chosen temperature and thus produce a "topped" mixture of acids, or to remove higher boiling acids having a boiling point higher than a second chosen temperature and thus produce a "tailed" mixture of acids, or to remove both lower and higher boiling acids and thus produce a "topped and tailed" mixture of acids.

In a preferred process according to the invention esterification of the fatty acid or fatty acid mixture with the lower alkanol (e.g. methanol) is effected by a procedure in which the fatty acid or fatty acid mixture and lower alkanol are passed in countercurrent flow through a column reactor provided with a plurality of esterification trays mounted one above another, each adapted to hold a predetermined liquid volume and a charge of solid esterification catalyst thereon, liquid downcomer means associated with each esterification tray adapted to allow liquid phase to pass down the column reactor from that esterification tray but to retain solid esterification catalyst thereon, and vapour upcomer means associated with each esterification tray adapted to allow vapour to enter that esterification tray from below and to agitate the mixture of liquid and solid esterification catalyst on that tray, in which the fatty acid or fatty acid mixture is supplied in liquid phase to the uppermost one of said plurality of esterification trays whilst the lower alkanol is supplied in vapour form beneath the lowermost one of said plurality of esterification trays, in which vapour comprising lower alkanol and water of esterification is recovered from an upper part of the column reactor, and in which a lower alkyl fatty acid ester or ester mixture is recovered from a lower part of the column reactor.

In such a procedure the water content of the lower alkanol vapour supplied to the column reactor should be less than about 5 mole % and the number of esterification trays and the reaction conditions should be selected so that the stream of lower alkyl fatty acid ester or esters has a low acid content of less than about 1 mole %, calculated on a lower alkanol free basis, and an ester content, also expressed on an alkanol free basis, of at least about 99 mole %.

The process of the invention utilises the vaporous stream of the lower alkanol to carry away water of esterification produced in the esterification reactor but without carrying with it significant quantities of the fatty acid or acids or of the lower alkyl fatty acid ester or esters.

The esterification conditions used in the column reactor will normally include use of elevated temperatures up to about 160° C., for example a temperature in the range of from about 80° C. to about 140° C., preferably in the range of from about 100° C. to about 125° C. Such operating temperatures will be determined by such factors as the thermal stability of the esterification catalyst, the kinetics of the esterification reaction and the vapour temperature of the lower alkanol fed to the base of the column reactor at the relevant inlet pressure. Typical operating pressures at the vapour inlet of the column reactor range from about 0.1 bar to about 25 bar. A liquid hourly space velocity through the column reactor in the range of from about 0.1 hr$^{-1}$ to about 10 hr$^{-1}$, typically from about 0.2 hr$^{-1}$ to about 2 hr$^{-1}$, may be used.

The fatty acid or fatty acid mixture is supplied in liquid form to an upper part of the column reactor or in admixture with lower alkanol, in solution in recycled ester product, or in solution in an inert solvent or diluent therefor. It is possible to pre-react the lower alkanol and the fatty acid or fatty acid mixture prior to introduction to the column reactor. The resulting reaction mixture contains a mixture of lower alkyl fatty acid ester or ester mixture, water, and lower alkanol Usually it is convenient to pre-react the lower alkanol and the fatty or fatty acid mixture to equilibrium in the presence of an acidic ion exchange resin containing —SO$_3$H and/or —COOH groups prior to introduction of the resulting equilibrium mixture to the column reactor.

In such an esterification process a vaporous mixture exits the column reactor as an overhead product. Provision may be made for scrubbing such vaporous mixture with lower alkanol in liquid form in order to wash traces of fatty acid ester and of fatty acid back into the column reactor. This overhead product from the column reactor can be condensed and treated in known manner to separate its constituents, the recovered water of esterification being rejected and the lower alkanol being recycled for re-use in as dry a form as is practicable within the relevant economic constraints. The lower the water content of the lower alkanol vapour that is supplied to the lowermost one of said esterification trays, the further towards 100% conversion to ester the esterification equilibrium reaction can be driven and the lower the residual acidity of the ester containing product recovered from the bottom of the column reactor will be. However, a balance may often have to be struck between the cost of providing, for example, a substantially dry lower alkanol for vaporisation into the column reactor, on the one hand, and the cost of providing and operating any additional downstream processing facilities that may be required to upgrade the ester product to the required quality if a less dry alkanol is used. This will vary from lower alkanol to lower alkanol and will depend upon the interaction between water and lower alkanol (e.g. azeotrope formation) and its effect upon alkanol/water separation. In any case, the water content of the lower alkanol vapour supplied to the reactor is less than about 5 mole %, and even more preferably is less than about 1 mole %.

The column reactor has a plurality of esterification trays. Although two or three trays may suffice in some cases, it will typically be necessary to provide at least about 5 up to about 20 or more esterification trays in the column reactor. Typically each esterification tray is designed to provide a residence time for liquid on each tray of from about 1 minute up to about 120 minutes, preferably from about 5 minutes to about 60 minutes.

The solid esterification catalyst may be a granular ion exchange resin containing —SO$_3$H and/or —COOH groups. Macroreticular resins of this type are preferred. Examples of suitable resins are those sold under the trade marks "Amberlyst", "Dowex", "Dow" and "Purolite", such as Amberlyst 13, Amberlyst 66, Dow C351 and Purolite C150.

Different solid esterification catalysts may be used on different trays of the column reactor. Moreover different concentrations of solid esterification catalyst can be used on different trays.

The charge of solid particulate or granular esterification catalyst on each tray is typically sufficient to provide a catalyst liquid ratio on that tray corresponding to a resin concentration of at least about 0.2% w/v for example, a resin concentration in the range of from about 2% w/v to about 20% w/v, preferably 5% w/v to 10% w/v, calculated as dry resin. Sufficient catalyst should be used to enable equilibrium or near equilibrium conditions to be established on the tray within the selected residence time at the relevant operating conditions. On the other hand not so much catalyst should be used on each tray that it becomes difficult to maintain the catalyst in suspension in the liquid on the tray by the agitation produced by the upflowing vapour entering the tray from below. For a typical resin catalyst a resin concentration in the range of from about 2% v/v to about 20% v/v, preferably 5% v/v to 10% v/v may be used.

The particle size of the catalyst should be large enough to facilitate retention of the catalyst on each tray by means of a screen or similar device. However, as larger catalyst particle sizes are more difficult to maintain in suspension and have lower geometrical surface area per gram, it is expedient to use not too large a catalyst particle size. A suitable catalyst particle size is in the range of from about 0.1 mm to about 5 mm.

One or more wash trays may be provided above the esterification trays in order to prevent loss of product, solvent and/or reagents from the column reactor.

In the column reactor the vapour upcomer means associated with each esterification tray may comprise a sparger positioned so that, in operation, it will lie below the surface of the mixture of liquid and solid esterification catalyst on that tray and so that vapour bubbles emerging therefrom will agitate said mixture of liquid and solid particulate catalyst. The sparger may be a ring sparger. At least one baffle means may be mounted in the vicinity of the sparger to enhance the mixing action thereof. For small scale operation a sparger on the axis of the column reactor under a cylindrical baffle can be used.

In one embodiment the sparger is a ring sparger and inner and outer annular baffle means are positioned in the vicinity of the sparger and define an upflow zone in the region of upflowing vapour bubbles and adjacent downflow zones within and outside the upflow zone.

It is important to avoid stagnant zones where solid esterification catalyst can settle out because this can lead to excessive formation of by-products or to occurrence of hot spots. Although mechanical stirrers can be provided on each tray to maintain the catalyst particles suspended in liquid, this adds somewhat to the complexity of the reactor. It is possible, however, by suitable design of the sparger and tray to ensure that the upflowing vapour provides sufficient agitation in passage through the liquid on the tray to maintain the catalyst particles in suspension. To achieve this end it is convenient that at least a part of the floor of one or more (and preferably all) of the esterification trays slopes towards a zone where there is turbulence caused by the upflowing vapour such as is to be found under the sparger. The angle of slope is preferably selected so as to be equal to or greater than the angle of repose of the solid particulate esterification catalyst under the liquid in the esterification tray. The adoption of such a slope will tend to ensure that all of the catalyst is in dynamic contact with the liquid during operation and that no stagnant zones of catalyst are formed. Such stagnant zones are undesirable because they can enable undesirable side reactions or even thermal runaways to occur in certain instances.

In a preferred apparatus the vapour upcomer means of one or more (and preferably all) of the esterification trays is or are provided with a liquid suckback preventer means.

A screen means may be provided on at least one esterification tray to hinder loss of solid esterification catalyst from that esterification tray via its associated downcomer means. In this way downward flow of the solid catalyst from one esterification tray to the next lower one can be substantially prevented.

Means may be provided for withdrawing or adding resin to one or more of the trays during operation of the column reactors. For example, a conduit having a down turned open end can extend into the interior of a respective tray with its open lower end positioned at a low point within the tray. By this means a slurry of catalyst and liquid can be withdrawn in controlled manner from the tray intermittently or continuously as desired or further catalyst can be introduced in slurry form to the trays, as desired. Catalyst withdrawn from a given tray can be reintroduced into the column reactor, either into the same tray or to a lower or higher one, possibly after being given a regeneration treatment.

In the hydrogenation step of the process of the invention lower alkyl fatty acid esters are hydrogenated under vapour phase hydrogenation conditions in which the composition of the gas stream is selected so that at all times the material in contact with the hydrogenation catalyst is above the dew point, preferably at least about 5° C. above the dew point. Suitable hydrogenation catalysts include known ester hydrogenation catalysts such as reduced copper oxide-zinc oxide (see GB-B-2116552 and WO-A-82/03854), and copper chromite, and promoted copper chromite catalysts. The preferred catalysts are reduced copper oxide-zinc oxide catalysts of the type disclosed in GB-B-2116552 and WO-A-82/03854. Such catalysts include reduced mixtures of copper oxide and zinc oxide derived from mixtures comprising, before reduction, (a) from about 10 to about 70 percent by weight CuO and about 90 to about 30 percent by weight ZnO, (b) from about 65 to about 85 percent by weight CuO and about 15 to about 35 percent by weight ZnO, and (c) from about 40 to about 50 percent by weight each of CuO and ZnO and 0 to 20 percent by weight of alumina. The preferred copper chromite catalysts are those containing from about 25 to about 45 percent by weight of copper and from about 20 to about 35 percent by weight of chromium, calculated as metal. Typical vapour phase hydrogenation conditions include use of temperatures of up to about 260° C., such as temperatures in the range of from about 140° C. to about 240° C., and pressures in the range of from about 5 bar to about 100 bar. Typically the $H_2$:ester mole ratio in the vaporous feed to the hydrogenation zone is at least about 200:1 up to about 2000:1 or more.

The hydrogenation mixture obtained by hydrogenating a lower alkyl fatty acid ester or mixture of esters contains, in addition to a fatty alcohol or fatty alcohol mixture, also lower alkanol, such as methanol. The methanol is separated in any known manner, as by distillation in one or more stages, from the fatty alcohol or alcohols to yield a fatty alcohol fraction suitable for use in the process of the invention. Such a fatty alcohol fraction typically contains, besides possibly a minor molar amount of methanol or other lower alkanol (usually less than about 5 mole %), a major molar amount of a fatty alcohol or alcohols (usually about 90 mole % or more) and a minor molar amount of unreacted lower alkyl fatty acid ester or esters (usually from about 0.5 mole % up to about 5 mole %).

In the hydrogenation step of the process of the invention vapour phase conditions are used. In order to maintain all components in the vapour phase two important factors are (a) the $H_2$:ester molar ratio of the vaporous mixture to the hydrogenation zone and (b) the temperature thereof. In general, the high the molecular weight of the lower alkyl fatty acid ester is, the less volatile it is and the higher its boiling point. Hence, for example, when using methyl laurate as a feedstock to the hydrogenation zone, a lower $H_2$:ester molar ratio and a lower inlet temperature to the hydrogenation zone can be used than when a higher boiling ester, such as methyl stearate, is to be hydrogenated. In practice a plant operator may wish to have the freedom to operate the process using fatty acids derived from different sources at different times. For example, he may wish to operate at different times using fatty acids from any of the common sources, such as tallow, lard, fish oil, coconut oil, rape seed oil or palm oil. A plant capable of handling such a range of acid feedstocks must be capable of hydrogenating the highest boiling methyl or other lower alkyl ester of a fatty acid that is likely to be used. Hence it must have an ester vaporisation section that can operate over a range of $H_2$:ester molar ratios and that can deliver to the hydrogenation zone a vaporous inlet mixture at the appropriate temperature, i.e. a higher inlet temperature and a higher $H_2$:ester molar ratio for methyl stearate, for example, than for methyl laurate.

The hydrogenation zone may comprise a single reactor operated under adiabatic conditions and containing a single bed of an ester hydrogenation catalyst, such as copper chromite or a reduced CuO-ZnO catalyst. In this case, however, the bed of catalyst must be sized so as to enable hydrogenation to be completed so far as possible by a single passage of the vaporous mixture therethrough at the design feed rate when operating at the lowest design temperature. In addition provision has to be made in designing the plant for any catalyst deactivation that may occur with ageing of the catalyst. If this approach is adopted then, with a catalyst charge that is sized for operation at a temperature suitable for a relatively low boiling ester, such as methyl laurate, it will be understood that, at the higher operating temperatures and higher $H_2$:ester molar ratios needed to maintain a high boiling ester, such as methyl stearate, in the vapour phase, hydrogenation occurs faster so that it is mainly the front end of the catalyst bed that is playing a part in the hydrogenation reactor, whilst the back end of the catalyst bed plays essentially no part. A disadvantage of this design approach is that, when operating with a high boiling ester, such as methyl stearate, the hot reaction mixture remains in contact with the catalyst for a significant time at the back end of the catalyst bed, although the hydrogenation reaction has effectively gone to completion, with the result that the conversion to by-products is correspondingly higher.

To overcome this problem it is proposed, in a preferred process according to the invention, to conduct hydrogenation using a hydrogenation zone having a plurality of beds, or sections of catalyst bed, of hydrogenation catalyst arranged in series which can be brought into use as required. In one arrangement the hydrogenation reactor has a main inlet and a main outlet, a plurality of beds of hydrogenation catalyst in the path of gas flowing between the main inlet and the main outlet, and one or more secondary flow connections each located between a respective pair of catalyst beds. the vaporous mixture containing hydrogen and lower alkyl fatty acid ester can be fed to the hydrogenation reactor by means of the main outlet whilst the reaction product is withdrawn either via the main outlet, so that all of the catalyst beds are used, or via one of the secondary flow connections, so that one or some only of the catalyst beds is or are used, depending upon the volatility of the ester, and hence upon the H₂:ester molar ratio and the inlet temperature of the vaporous mixture. Alternatively the reaction mixture can be withdrawn from the main outlet whilst the vaporous mixture is fed to one of the secondary flow connections. any catalyst beds which are not in active use are maintained under an appropriate pressure of hydrogen. In this way the plant operator can readily select the appropriate number of beds of catalyst to suit the nature of the fatty acid feedstock currently being used.

In the first transesterification zone the fatty alcohol fraction is subjected to transesterification. Such transesterification can be carried out in the absence of added catalyst by heating to elevated temperature, for example to a temperature of about 250° C. or higher. Normally, however, it will be preferred to effect transesterification in the first transesterification zone in the presence of a transesterification catalyst Any known transesterification catalyst may be used. Examples include alkyl titanates, alkali metal alkoxides, and metallic tin and stannous hydroxide. Although acids, such as sulphuric acid and sulphonic acids, have been proposed as liquid phasetransesterification catalysts in the prior art, the use of such catalysts is best avoided since there is a risk of the fatty alcohol product becoming contaminated with sulphurous impurities. Other transesterification catalyst systems which have been proposed, but are not preferred, include bases, compounds of alkali and alkaline earth metals, water, and metals such as zinc, cadmium, lead and their compounds. It is also contemplated that acidic resins containing —SO₃H and/or —COOH groups or basic resins containing substituted ammonium groups can be used as transesterification catalysts.

A particularly preferred class of transesterification catalyst is the alkyl titanates. Any alkyl titanate may be added as catalyst but, as the alkyl titanate will itself participate in ester interchange, the alkoxide radicals originally present in the alkyl titanate will tend to undergo exchange with alkoxide radicals derived from the fatty alcohol or alcohols during the operation of the process of the invention.

Another particularly preferred class of transesterification catalyst is the alkali metal alkoxides, such as sodium methoxide or sodium ethoxide. Again exchange of alkoxide radicals in the catalyst with alkoxide radicals derived from the fatty alcohol or alcohols will tend to occur with time in the first transesterification zone. Alternatively there may be used an alkali metal alkoxide derived from the fatty alcohol product itself, or from one or more of them if a mixture of fatty alcohols is to be produced.

The transesterification conditions used in the first transesterification zone will to a large extent depend upon the use or otherwise of a transesterification catalyst and upon the activity of the transesterification catalyst. Although the use of elevated pressures is not ruled out, it will normally be preferred to operate at a substantially atmospheric pressure or below, for example a pressure in the range of from about 0.1 bar to about 1.2 bar. In this way the vaporisation of methanol or other lower alkanol is facilitated during the course of the transesterification reaction. Removal of the lower alkanol during transesterification drives the transesterification reaction towards completion.

When using an alkyl titanate a temperature of up to about 240° C., such as a temperature in the range of from about 120° C. to about 200° C., is typically used in the first transesterification zone, for example a temperature of from about 170° C. to about 180° C. Alkali metal alkoxides enable use of lower operating temperatures, e.g. in the range of from about 40° C. to about 100° C., but normally require introduction of extra processing steps as will be further explained below.

Similar transesterification conditions can be used in the second transesterification zone. A transesterification catalyst will normally be used, such as one of those listed above for use in the first transesterification zone. However, it is also contemplated to operate without such a catalyst. It will usually be preferred to employ in the second transesterification zone a superatmospheric pressure, for example a pressure of from about 1.5 bar to about 50 bar, in order to maintain the lower alkanol (e.g. methanol) in the liquid phase in the second transesterification zone.

An advantage of the use of an alkyl titanate as transesterification catalyst in the first and second transesterification zones is that the subsequent distillation and/or evaporation steps can be conducted without prior removal of the catalyst. However, when using an alkali metal alkoxide as transesterification catalyst, it is preferable to neutralise the catalyst prior to distillation and/or evaporation. Conveniently this neutralisation step can be effected by passing the catalyst containing material through a bed of an ion exchange resin containing —SO₃H and/or —COOH groups, thus removing the alkali metal from the liquid mixture:

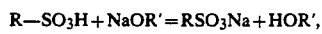

$$R—SO_3H + NaOR' = RSO_3Na + HOR',$$

where R represents the resin and —OR' represents an alkoxide radical.

A further advantage of the use of alkyl titanates is that the catalyst remaining in the distillation residue (ii) or in the relatively involatile residue (b) can be used to form at least a part of the transesterification catalyst used in the first transesterification zone. The balance of any amount of catalyst required can then be supplied by make up alkyl titanate Control of "heavies" in the process can be achieved by purging a part of the relatively involatile residue of (b); the remainder of this relatively involatile residue can be recycled for use in the first transesterification zone.

When using an alkali metal alkoxide as transesterification catalyst, on the other hand, there will usually be no residual catalyst in the relatively involatile residue (ii) as neutralisation will usually be practised prior to any distillation step. Similarly, if a resin catalyst is used as a transesterification catalyst, there will be no catalyst dissolved in the relatively involatile residue (ii). Hence recycle of the relatively involatile residue has no benefit in these cases and the relatively involatile residue (ii) can be purged from the plant and used as fuel.

If an alkyl titanate transesterification catalyst is used, then the evaporation and distillation steps downstream from the second transesterification zone can be carried out without prior removal of the catalyst. In this case it is best to operate with as short residence times as possible in these steps so as to minimise the risk of substantial reversion of the transesterification reaction with consequent re-formation of wax esters in these steps. Hence it is preferred to effect this evaporation step by flash distillation so as to minimise the residence time in this step and to effect this distillation step, for similar reasons, in a falling film or wiped film evaporator.

Distillation of the substantially lower alkanol free mixture to yield overhead fraction (i) and distillation residue (ii) and of the liquid residue to produce overhead product (a) and relatively involatile residue (b) are normally effected at or near atmospheric pressure or below, for example at a pressure in the range of from about 0.005 bar to about 1.2 bar.

Figure 1B:
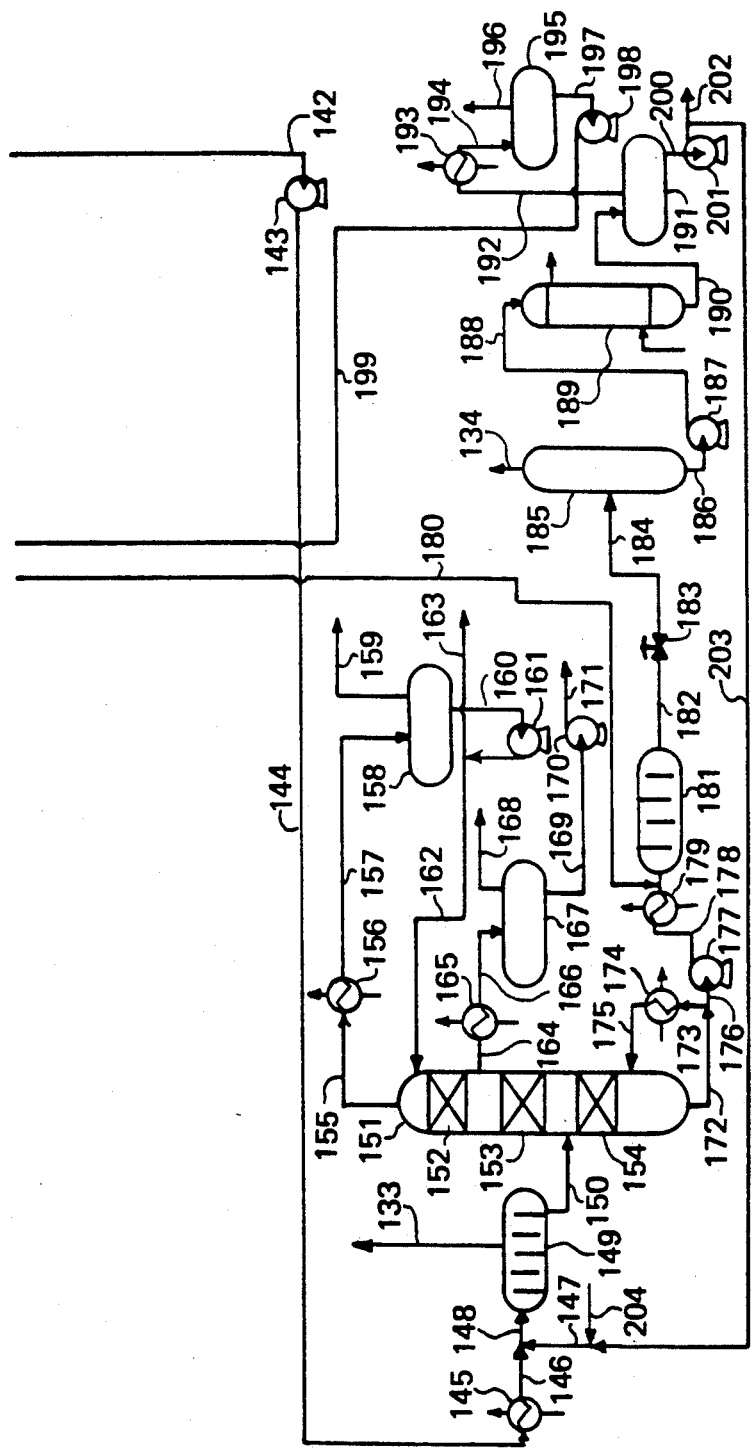
Figure 2:
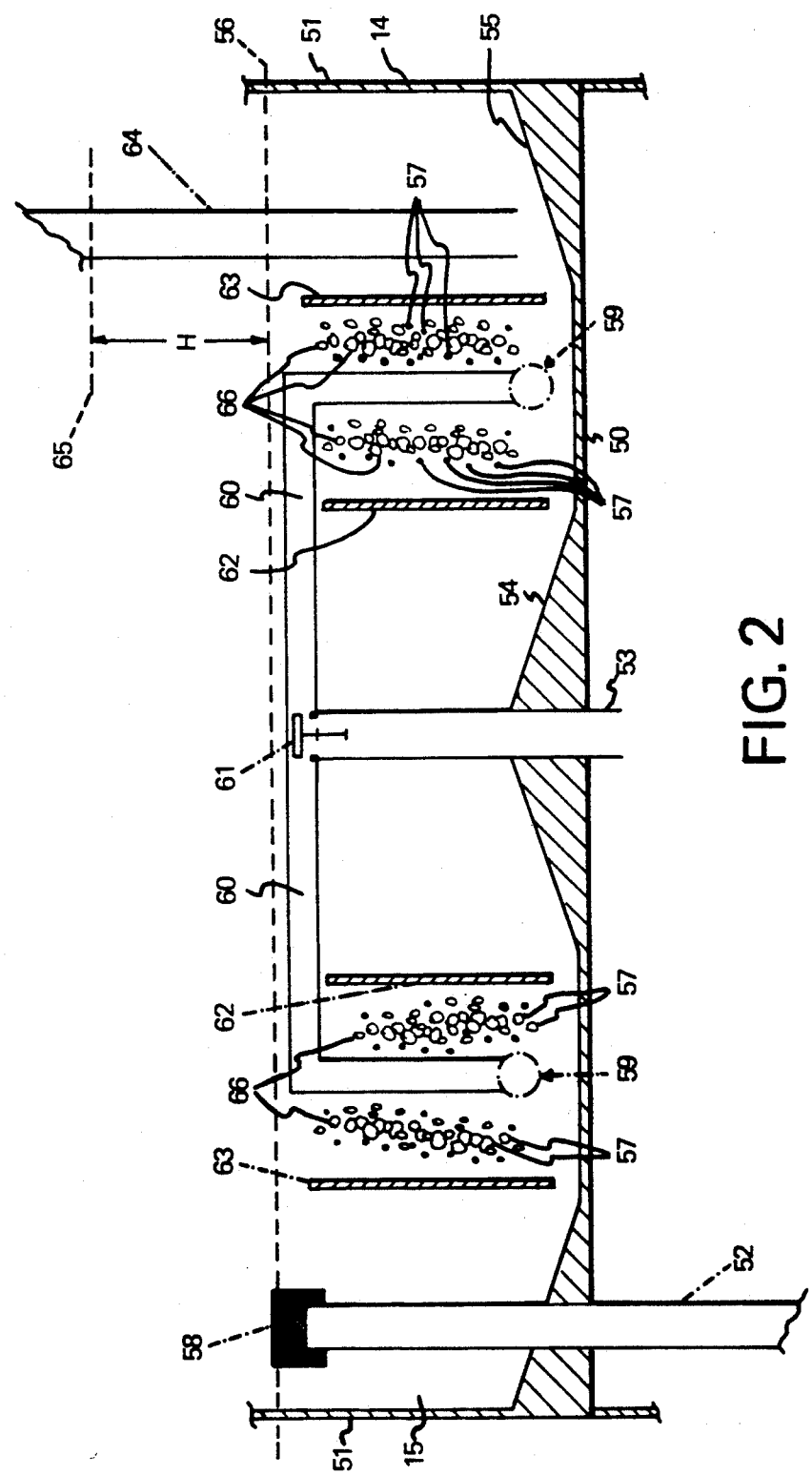
Figure 3:
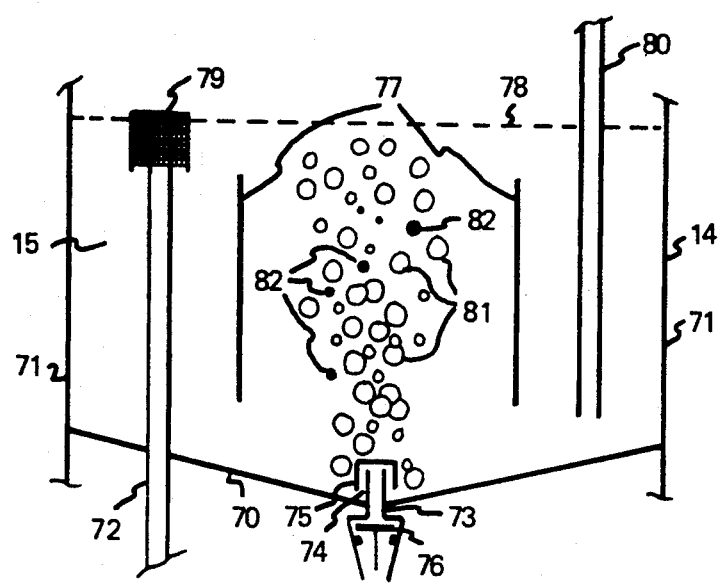
Figure 4:
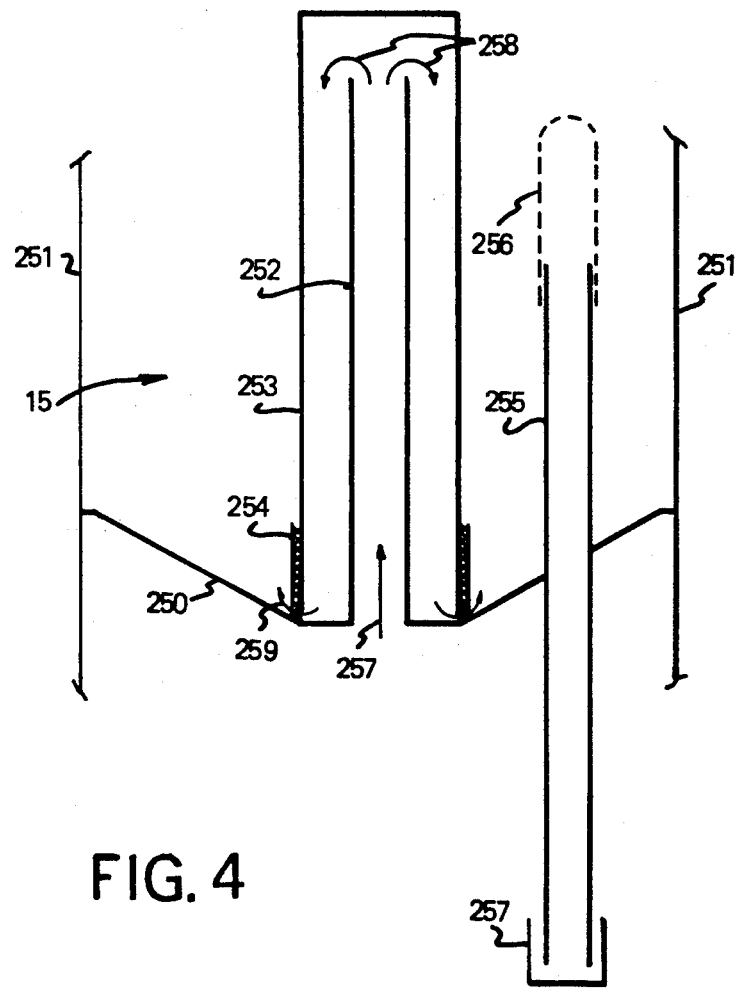
Figure 5A:
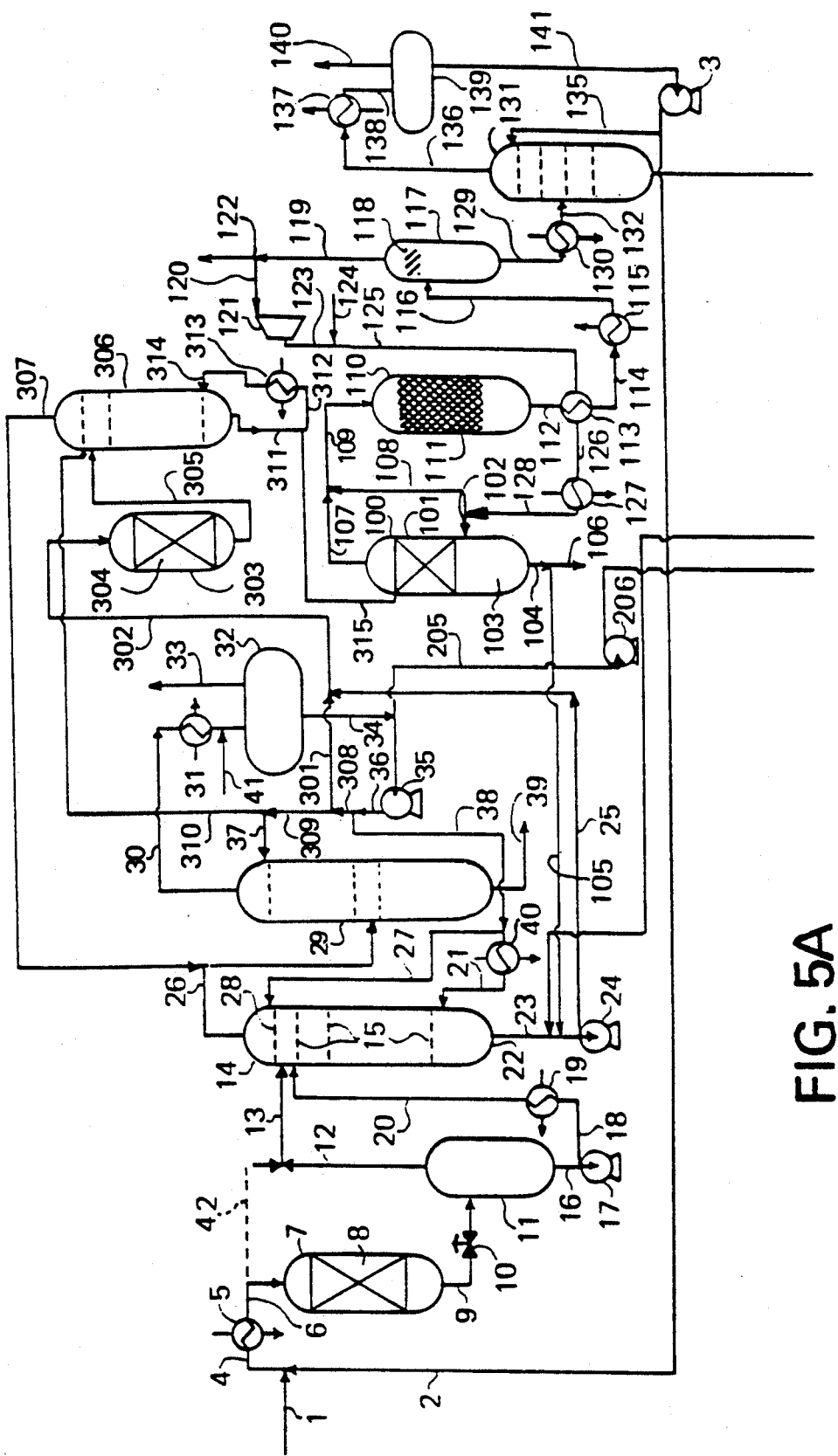
Figure 6:
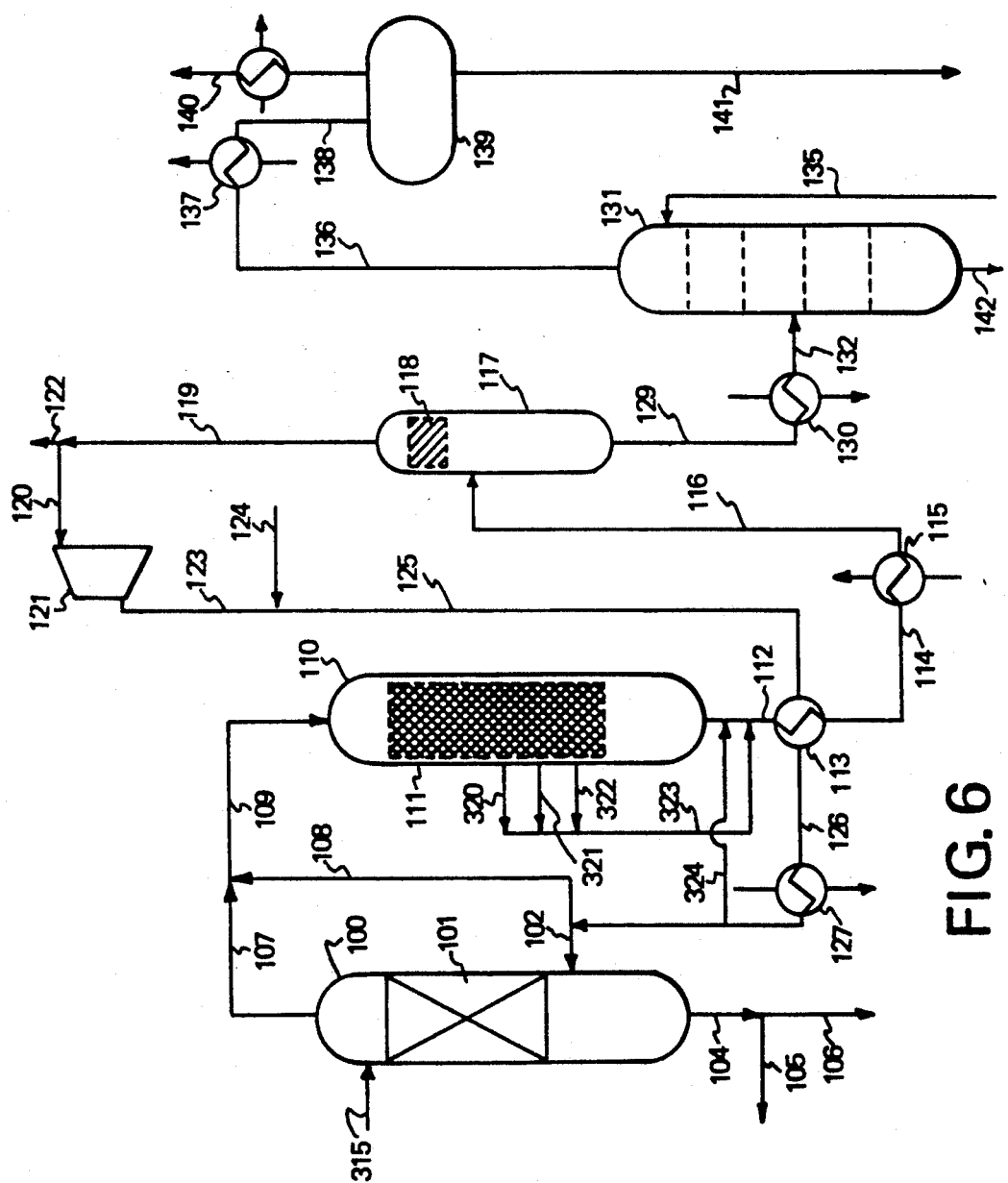
Figure 8:
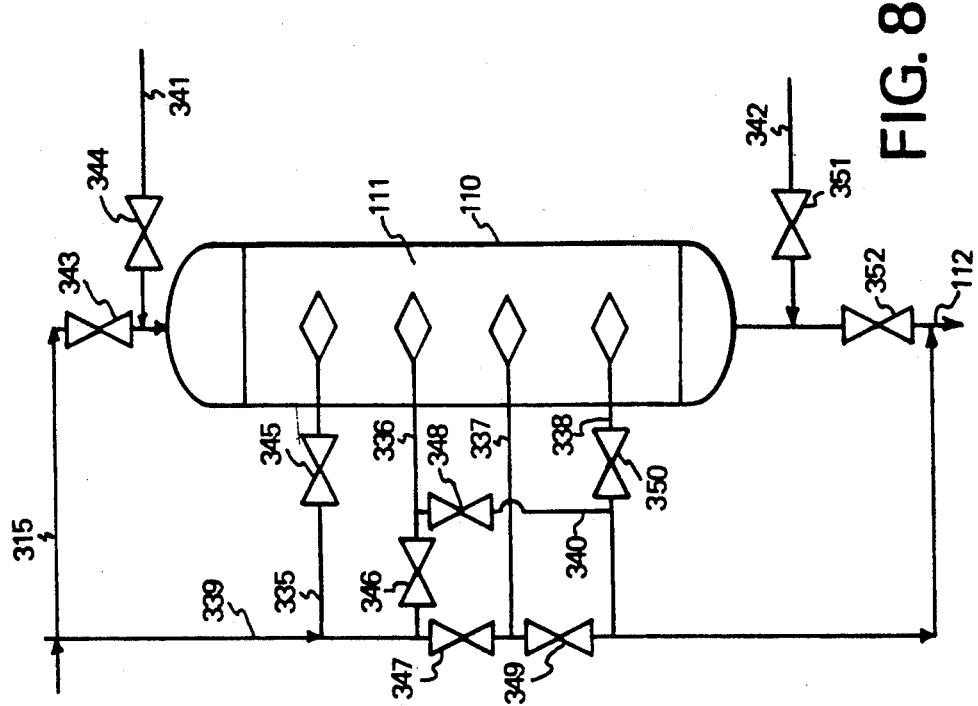
Figure 7:
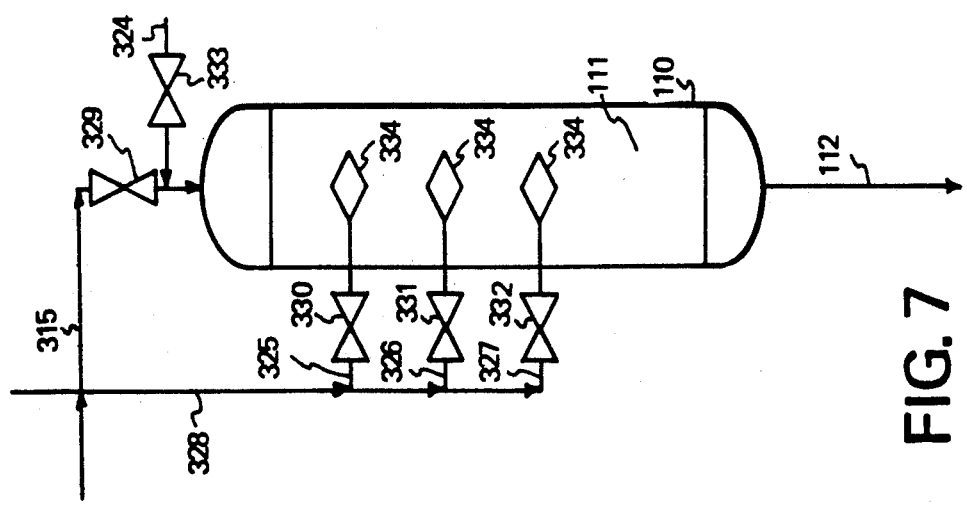
Figure 10:
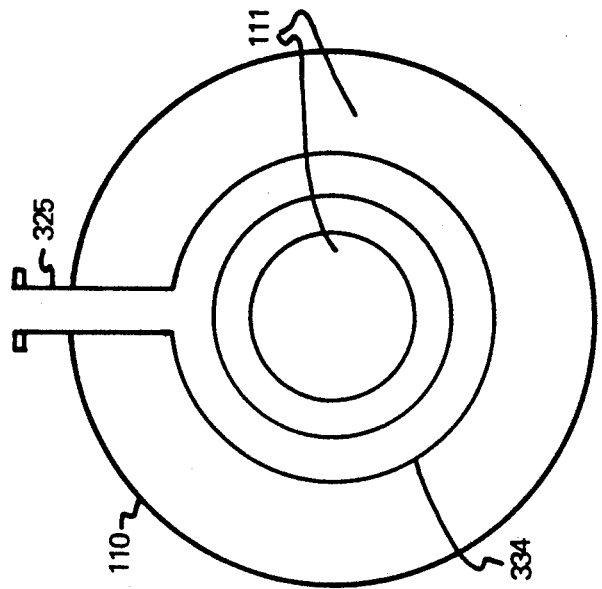
Figure 9:
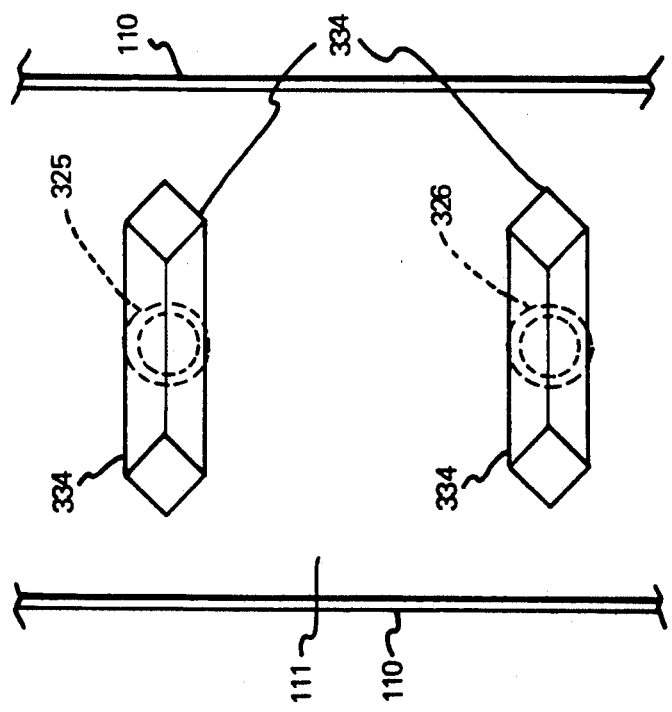

In order that the invention may be clearly understood and readily carried into effect some preferred forms of alcohol production plant designed to operate according to the teachings of the present invention will now be described, by way of example only, with reference to the accompanying drawings, in which:

FIG. 1A and B is a flow diagram of a plant for the production of fatty alcohols constructed in accordance with the teachings of the invention;

FIGS. 2 to 4 show details of parts of two designs of esterification reactor that can be used in the plant of FIG. 1.;

FIG. 5A and B is a flow diagram of another plant;

FIG. 6 shows part of a modified form of plant designed to be capable of operating using different fatty acid feedstocks;

FIGS. 7 and 8 each show part of respective further forms of fatty alcohol production plant;

FIG. 9 is a vertical section through a modified form of hydrogenation reactor for use in a fatty alcohol production plant; and FIG. 10 is a horizontal section through the reactor of FIG. 9.

It will be understood by those skilled in the art that the drawings are diagrammatic and that further items of equipment such as reflux drums, pumps, vacuum pumps, temperature sensors, pressure sensors, pressure relief valves, control valves, flow controllers, level controllers, holding tanks, storage tanks, and the like may be required in a commercial plant. The provision of such ancillary items of equipment forms no part of the present invention and is in accordance with conventional chemical engineering practice.

Referring to FIG. 1 of the drawings, a fatty acid mixture is supplied to the plant in line 1 and is admixed with recycled methanol in line 2, which is pumped by pump 3, to form a mixed feed to the plant in line 4. The fatty acid mixture is, for example, a mixture of fatty acids obtained by hydrolysis of a naturally occurring triglyceride, e.g. coconut oil, followed by "topping and tailing". Such a fatty acid mixture contains approximately 65 mole % dodecanoic acid, 25 mole % tetradecanoic acid, and 10 mole % hexadecanoic acid. The mixed feed in line 4 flows on to a heat exchanger 5, in which its temperature is raised to 110° C. The heated acid/methanol mixture flows on in line 6 into primary esterification reactor 7, which contains a charge 8 of an ion exchange resin containing sulphonic acid and/or carboxylic acid groups, such as Amberlyst 13. (The word "Amberlyst" is a trade mark). The pressure in reactor 7 is 5 bar.

In reactor 7 part of the acid mixture is esterified by reaction with methanol to yield a corresponding mixture of methyl fatty acid esters. There exits from reactor 7 in line 9 a mixture of methyl esters, unreacted fatty acid, water produced by esterification and unreacted methanol. This mixture passes through a pressure let down valve 10 into a vapour/liquid separator 11. A vapour phase comprising methanol and water is fed at 1.3 bar by way of lines 12 and 13 to an upper part of an esterification reactor 14. Reactor 14 is provided with a number of esterification trays 15; two possible forms of esterification tray 15 are illustrated in FIGS. 2 and 3 and will be described in greater detail below. In reactor 14 of FIG. 1 there are six esterification trays 15 (not all of which are shown); however, a greater or lesser number of such trays may be provided, depending upon the nature of the fatty acid or fatty acid mixture and the reaction conditions selected.

The liquid phase from vapour/liquid separator 11 is fed by way of line 16, pump 17 and line 18 to heat exchanger 19, in which it is heated by steam to a temperature of up to 150° C., (e.g. 120° C.), and then by means of line 20 to reactor 14 at a point below the entry point of line 13.

In reactor 14 the downflowing unreacted fatty acids in the mixture in line 20 pass downwardly from each esterification tray 15 to the next lower tray 15 against an upflowing current of vapour comprising methanol and water of esterification, i.e. water produced as a result of the esterification reaction. Dry methanol vapour is supplied to reactor 14 in line 21. Each esterification tray 15 holds a charge of an acidic ion exchange resin, such as a resin containing sulphonic acid groups. Amberlyst 13 is a suitable resin. (Amberlyst is a trade mark). In passage down column 14 any unreacted free acid encounters progressively drier methanol vapour on each tray 15. By designing each tray 15 to provide an appropriate liquid hold up, it is possible to regulate the residence time on each tray 15. By selecting a suitable number of trays 15 it is further possible to design reactor 14 so that essentially no free fatty acid remains in the liquid passing downwards from the bottom tray 15 into the sump 22 of reactor 14. Methyl ester product (i.e. a mixture of methanol and methyl esters derived from the mixed fatty acids supplied in line 4) is removed from sump 22 in line 23 and pumped onward by pump 24 via line 25 to the hydrogenation stage of the plant. A mixture of methanol vapour and the water released in the esterification reaction is recovered overhead from reactor 14 in line 26. Liquid methanol is supplied in line 27 to an upper part of reactor 14 above the point of connection of line 13 to provide liquid methanol on wash tray 28.

The vapour in line 26 is fed to a methanol/water separation column 29 which is operated at 1.3 bar and at a head temperature of 70° C. Dry methanol vapour is recovered overhead in line 30 and is condensed in condenser 31. The resulting condensate is collected in drum 32 which is vented as indicated at 33. Dimethyl ether produced as byproduct isvented in line 33. Methanol which would otherwise be lost along with the dimethyl ether can be recovered by providing a chilled condenser (not shown) in line 31. Part of the condensed methanol is recycled to column 29 from drum 32 as a reflux stream in line 34 by means of pump 35 and lines 36 and 37. Part of the condensed methanol is pumped in line 205 by high pressure pump 206 to line 180 for use in the second transesterification reactor. The remainder is pumped back for re-use in line 38.

The sump product from column 29 consists essentially of water. This is withdrawn in line 39. Part is recycled to column 29 by way of a steam heated reboiler (not shown); the remainder is passed on for effluent treatment.

Some of the dry methanol in line 38 is passed through vaporiser 40 to provide the stream of dry methanol vapour in line 21. The rest flows on to provide the reflux stream in line 27. Make-up methanol for the plant is supplied through line 41 to reflux drum 32.

In a modification of the plant of FIG. 1 reactor 7 and vapour/liquid separator 11 are omitted and the mixture of fatty acids and optionally some methanol is fed by way of line 42 to line 13. In this case the balance of the recycle methanol in line 2 is passed through vaporiser 40 and the number of esterification trays 15 in reactor 14 is increased by (say) 4 or 5.

FIG. 2 illustrates one form of construction of a tray 15 of reactor 14 of the plants of FIG. 1. A horizontal diaphragm or partition 50 extends within wall 51 of reactor 14 and closes off the cross section of reactor 14 completely except for a downcomer 52 for liquid and a vapour upcomer 53. Partition 50 has an axial frusto-conical part 54 surrounding vapour upcomer 53 and an annular sloping portion 55 adjacent wall 51. Tray 15 can thus retain a volume of liquid whose surface is indicated at 56 and whose volume is determined by the height of the overflow level of downcomer 52 above the partition 50. Each tray 15 also supports a charge of an acidic ion exchange resin containing —$SO_3H$ groups, such as Amberlyst 13, whose particles are indicated diagrammatically at 57. Such ion exchange particles are kept in suspension in the liquid on tray 15 as a result of agitation caused by the upcoming vapour as will be described below. To prevent escape of ion exchange particles 57 with the liquid overflowing down downcomer 52 the top of downcomer 52 is provided with a screen 58. The slope of frusto-conical part 54 and of sloping portion 55 is equal to or greater than the angle of repose of the Amberlyst 13 or other solid particulate esterification catalyst under the liquid on esterification tray 15.

Vapour upcomer 53 conducts upcoming vapour to a circular sparger 59, which surrounds frusto-conical part 54, by way of spider tubes 60. Suckback of liquid down upcomer 53 is prevented by means of an anti-suckback valve 61.

Annular draught shrouds or baffles 62 and 63 are positioned within the body of liquid on tray 15, one inside and one outside circular sparger 59 to promote agitation of the liquid/resin suspension by the upcoming vapour. The vertical extent of shrouds 62 and 63 is not critical but should generally be between one third and three quarters of the vertical height between diaphragm 50 and liquid surface 56. It is preferred that shrouds 62 and 63 should be placed in a symmetrical or near symmetrical vertical position. In the annular zone between shrouds 62 and 63 the liquid flow is generally upward whilst inside shroud 62 and outside shroud 63 the general direction of liquid flow is downward. Preferably the area of the annular zone between shrouds 62 and 63 approximately equals the sum of the areas inside shroud 62 and outside shroud 63.

Reference numeral 64 indicates a downcomer from the next tray above the one illustrated in FIG. 2. The liquid level in downcomer 64 is indicated at 65, the height H of this liquid level above liquid level 56 on tray 15 being fixed by the liquid level on the tray which feeds downcomer 64 (i.e. the tray above the illustrated tray 15) plus the pressure drop through the sparger 59 on that tray (i.e. the one above the illustrated tray 15) and the frictional pressure drop.

In operation of reactor 14 a liquid containing a fatty acid or mixture of fatty acids is typically passed downwards in countercurrent to an upflowing vaporous stream of lower alkanol e.g. methanol. Each tray 15 acts as an esterification zone containing a respective charge of esterification catalyst which catalyses the esterification reaction and the release of water of esterification. Under the countercurrent conditions prevailing in the reactor 14 such water of esterification is vaporised and carried upwards through reactor 14 with the upflowing lower alkanol vapour. The liquid passes downwards from one tray 15 to the next downward tray 15 and the free acid concentration in the liquid on each tray 15 is lower than the corresponding acid concentration in the liquid on the next higher tray 15. In addition the liquid encounters drier and drier lower alkanol vapour on each tray 15 as it passes down through reactor 14. In this way the equilibrium of the esterification reaction is pushed further towards ester formation, the reverse hydrolysis reaction being effectively suppressed because the water concentration in the liquid on the trays 15 decreases from tray to tray in the downward direction.

By selecting a suitable number of trays 15 in column 14 and designing each tray 15 to provide a sufficient liquid hold up to provide the requisite residence time on each tray it is possible to design reactor 14 so that the product in line 25 contains less than about 1 mole % of fatty acid, together with fatty acid esters and lower alkanol as its principal components. By providing an adequate upflow rate for lower alkanol vapour the agitation caused by the vapour bubbles 66 emerging from circular sparger 59, coupled with the liquid circulation induced by the presence of draught shrouds 62 and 63, can suffice to maintain the acidic ion exchange resin particles sufficiently in suspension for esterification to proceed successfully. The surfaces of sections 54 and 55 slope towards the zone under the sparger 59 and ensure that there are no stagnant zones where significant quantities of resin can settle out of suspension. (It will be appreciated that, although FIG. 2 only shows resin particles 57 in suspension in the zone between draught shrouds 62 and 63, they would in practice be present in suspension in the liquid phase outside this zone). If necessary, the volume of the upflowing vapour can be boosted by inert gas or by other vaporisable inert material, conveniently an inert material that is a byproduct of the process. For example, it is often found that an ether is found amongst the byproducts, as acidic catalysts can promote formation of an ether from the alcohol used. Thus dimethyl ether is a potential byproduct if methanol is used as the alcohol, whilst diethyl ether can be formed in reactor 14 if ethanol is the alcohol used; either material can be used, if necessary, to boost vapour upflow to provide additional agitation on trays 15 or to provide additional vapour to carry away water of esterification.

In FIG. 3 there is illustrated an alternative design of esterification tray 15 suitable for use in a relatively small scale reactor 14. In this case a frusto-conical partition or diaphragm 70 extends within wall 71 of reactor 14 and closes off the cross section of reactor 14 completely except for a downcomer 72 for liquid and a vapour upcomer 73. The slope of frusto-conical diaphragm 70 is equal to or greater than the angle of repose of the solid particulate catalyst under the liquid present on tray 15. The vapour upcomer 73 includes an axial sparger 74 provided with a bubble cap 75 and is fitted with an anti-suckback valve 76. Optionally bubble cap 75 can be surrounded by a mesh screen (not shown) to prevent ingress of catalyst particles interfering with the operation of valve 76. A cylindrical baffle 77 surrounds sparger 74 symmetrically and is positioned beneath the liquid level 78, the height of which is determined by the height of the upper end of downcomer 72. A screen 79 is fitted to the top of downcomer 72 to retain solid esterification catalyst, e.g. Amberlyst 13, on tray 15. Reference numeral 80 indicates the downcomer from the next higher esterification tray 15 (not illustrated). In a similar manner to that described in relation to FIG. 3 the bubbles 81 of vapour agitate the liquid on tray 15 and maintain particles 82 of catalyst in suspension. Baffle 77 defines an upflow zone within baffle 77 and a downflow zone outside baffle 77. Preferably the areas of the two zones are substantially equal. This design ensures that, so far as is possible, no stagnant zones where catalyst particles can sediment are formed.

If desired the feed line 20 or 13 in the plant of FIG. 1 can be arranged to discharge onto a tray, similar to tray 15 of FIG. 2 or FIG. 3, which does not hold a charge of ion exchange resin. One or more alkanol wash trays may be provided above the connection of feed line 20 or 13 so that the vapours are scrubbed with a minor amount of liquid alkanol before exiting reactor 14 in line 26 so as to limit the amount of acid or ester to traces therein.

Reverting to FIG. 1, the methyl ester product in line 25 is fed to the top of a vaporiser 100 and is distributed over the packing 101 in vaporiser 100. In vaporiser 100 the descending organic material is vaporised into an ascending stream of hot hydrogen supplied in line 102. Any liquid that collects in sump 103 of vaporiser 100 is recycled in lines 104 and 105 to the suction side of pump 24. Provision is made for purging a small stream in line 106 in order to limit build-up of "heavies" in the organic material supplied to vaporiser 100. Typically vaporiser 100 is operated at a temperature of about 205° C. and at a pressure of about 41 bar.

A vaporous organic material/hydrogen stream is recovered overhead from vaporiser 100 in line 107 and is admixed with further hot hydrogen from bypass line 108 so as to dilute this vaporous stream somewhat and to maintain the resulting diluted mixture in line 109 at a temperature above its dew point, preferably at least about 5° C. above its dew point. From line 109 the vaporous mixture enters hydrogenation reactor 110 which contains a charge 111 of a reduced copper oxide-zinc oxide catalyst of the type disclosed in GB-B-2116552. A typical catalyst contains, before reduction, about 35 weight % of copper oxide and about 65 weight % of zinc oxide.

In passage through the charge 111 of hydrogenation catalyst a high proportion of the methyl esters is converted to fatty alcohols and methanol. Accordingly there exits from hydrogenation reactor 110 in line 112, at a temperature of 214° C. and at a pressure of 40.7 bar, a vaporous reaction mixture containing fatty alcohols, methanol, a minor amount of unreacted methyl esters and minor amounts of byproducts. This mixture is passed through a gas/gas heat exchanger 113 and on through line 114 to a cooler 115. The cooled reaction mixture flows on in line 116 to a gas/liquid separator 117 which contains a demister pad 118 or other vapour/liquid separation device.

A hydrogen-rich stream exits gas/liquid separator 117 in line 119 and is passed by line 120 to the suction side of gas circulator 121. A purge gas stream is taken in line 122 in order to limit the build-up of inert gases in the circulating hydrogen. Make-up hydrogen gas is admixed with the compressed gas in line 123, such make-up hydrogen gas being supplied from line 124. The combined stream of make-up and recirculated gas is fed in line 125 to the other side of gas/gas heat exchanger 113 and then via line 126 to gas super-heater 127 to provide in line 128 the source of hot hydrogen for lines 102 and 108.

The make-up hydrogen stream in line 124 can be produced in conventional manner from synthesis gas followed by a water gas shift reaction, $CO_2$ removal and, if desired, further purification by pressure swing absorption. It may contain one or more inert gases, such as nitrogen, methane and argon.

A liquid condensate is removed from gas/liquid separator 117 in line 129, is partially vaporised in heat exchanger 130 and fed to methanol recovery column 131 in line 132 via a pressure let down valve (not shown). Methanol vapour from lines 133 and 134 of the product alcohols recovery and refining stage of the plant (which is to be described further below) is admixed with the material in line 132 prior to entry to methanol recovery column 131. A methanol reflux stream is supplied to column 131 in line 135.

Methanol vapour from column 131 is taken via line 136, condenser 137 and line 138 to methanol condensate drum 139 in which it accumulates. Vent line 140 allows any volatiles to escape to the flare stack of the plant via a vent condenser (not shown). Methanol is withdrawn from drum 139 in line 141 by pump 3 to provide the recycle streams in lines 2 and 135.

A substantially methanol free stream of fatty alcohols, containing a minor amount of unreacted methyl fatty acid esters, is pumped via line 142 from the bottom of column 131 by pump 143 to form the fatty alcohol fraction stream in line 144 supplied to the product alcohol recovery and refining stage of the plant.

The crude fatty alcohol stream in line 144 contains a minor amount of unconverted methyl esters, besides minor amounts of by-product alkanes, unknowns and "heavies". The crude fatty alcohol stream passes through heat exchanger 145 in which its temperature is adjusted to about 160° C. to about 200° C., preferably about 170° C. to about 190° C., e.g. 190° C. The hot stream in line 146 is admixed with a mixture of fresh and recycled ester interchange catalyst (transesterification catalyst), e.g. an alkyl titanate, supplied in line 147 and passes on in line 148 into a first ester interchange reactor 149 which provides a first transesterification zone. Reactor 149 is designed so as to provide a residence time therein in the range of from about 10 minutes up to about 120 minutes, preferably from about 15 minutes to about 60 minutes. The length of the residence time depends upon the temperature of the stream in line 148 and in reactor 149 as well as the effective concentration of the alkyl titanate supplied in line 147. In reactor 149 the methyl esters of the fatty acids present in the feed stream in line 148 are converted to wax esters, i.e. fatty alcohol esters of the acid moieties of the methyl esters, by transesterification of the methyl esters with product fatty alcohols. Most of the methanol formed by transesterification is recovered as a vapour in line 133 from the vapour space in vessel 149 and is recycled for admixture with the material in line 132 as described above.

The product from the first ester interchange reactor 149 contains, besides a major molar amount of product alcohols, also minor molar amounts of alkane by-products, wax esters and "heavies", as well as traces of methanol. It is passed via line 150 into a product column 151 which is provided with three beds of structured packing 152, 153 and 154. Light ends, consisting mainly of alkane by-products, as well as traces of methanol, are recovered overhead in line 155 and are condensed by means of condenser 156. The resulting condensate in line 157 accumulates in reflux drum 158 which is vented to a vacuum pump (not shown) operating at 0.005 bar by line 159. Some alkanes are returned to product column 151 via line 160, pump 161 and line 162 to provide a reflux stream, whilst the net production of alkanes passes via line 163 to storage.

Product alcohols are withdrawn as vapour from product column 151 in line 164 and are condensed by means of condenser 165. The condensate passes on in line 166 to product drum 167 which is vented to a vacuum unit (not shown) by line 168. Liquid product alcohols are passed via line 169, pump 170 and line 171 to product storage.

Bottoms product is withdrawn from product column 151 in line 172 and passed via line 173 to a falling film reboiler 174 which is operated at a temperature in the range of from about 210° C. to about 245° C., e.g. 240° C. The heated material from reboiler 174 is recycled to product column 151 in line 175. Part of the bottoms product is withdrawn in line 176 and is pumped by pump 177 via line 178 to heat exchanger 179. Excess methanol from line 180 is admixed with the hot bottoms product from heat exchanger 179. The quantity of methanol admixed via line 180 is typically at least about 5 times the stoichiometric quantity equivalent to the wax esters present in the bottom product up to about 100 times this stoichiometric quantity, for example about 80 times the stoichiometric quantity. In this way the equilibrium between wax esters and methanol, on the one hand, and methyl fatty acid esters, fatty alcohol and excess methanol, on the other hand, is shifted away from wax ester formation towards methyl fatty acid ester formation.

In heat exchanger 179 the temperature of the bottoms product, which still contains alkyl titanate transesterification catalyst, is adjusted. The mixture of hot bottoms product and excess methanol passes on to a second ester interchange reactor 181 which provides a second transesterification zone and is designed to provide a residence time of from about 30 minutes to about 240 minutes, preferably from about 60 minutes to about 180 minutes, e.g. about 120 minutes. The temperature in reactor 181 lies in the range of from about 160° C. to about 195° C., e.g. about 180° C. The size, and hence the residence time, selected for reactor 181 should be sufficient to allow the ester interchange to proceed to equilibrium at the temperature selected. The pressure in reactor 181 is typically about 42 bar. From second ester interchange reactor 181 the resulting transesterification product mixture is fed via line 182 through a pressure let down valve 183 to reduce its pressure to about 1.3 bar. It then continues in line 184 to a heated flash vessel 185. Methanol vapour is recovered overhead in line 134 and is admixed, as described above, with the material in line 132.

The residual liquid phase exits flash column 185 in line 186 and is pumped by pump 187 through line 188 via a pressure let down valve (not shown) to falling film evaporator 189 which is operated at a maximum temperature of about 240° C. and at a pressure of about 0.005 bar. A mixture of vapour and liquid exits falling film evaporator 189 in line 190 and passes into separation drum 191. The vapour is recovered in line 192 and condensed by condenser 193. The resulting condensate is passed in line 194 to drum 195 which is connected to a vacuum system (not shown) by line 196. The liquid condensate, which comprises a mixture of product fatty alcohols, methyl esters, some methanol and traces of by-products, is recovered in line 197 and pumped by pump 198 to form a recycle stream in line 199.

The liquid from drum 191 is passed by line 200 and pump 201 either for waste disposal via line 202 or for recycle via line 203 to line 147.

Fresh alkyl titanate transesterification catalyst can be added as required via line 204.

Line 205 and pump 206 provide the methanol for line 180.

The approximate flow rates of various of the streams expressed in molar units are summarised in Table 1 below:

TABLE 1

| Component | Line No. | | | | | | | | | | | |
|---|---|---|---|---|---|---|---|---|---|---|---|---|
| | 1 | 2 | 9 | 21 | 26 | 27 | 39 | 23 | 199 | 25 | 109 | 124 |
| Hydrogen | — | — | — | — | — | — | — | — | — | — | 48942.1 | 212.6 |
| Methane | — | — | — | — | — | — | — | — | — | — | — | — |
| Methanol | — | 202.6 | 152.6 | 200.0 | 282.1 | 10.0 | 0.5 | 27.0 | trace | 27.0 | 1003.8 | — |
| Water | — | 2.6 | 52.6 | — | 104.0 | — | 104.0 | 0.1 | — | 0.1 | 23.6 | — |
| Fatty Acids | 100 | — | 50.0 | — | — | — | — | 0.5 | — | 0.5 | 0.5 | — |
| Methyl Esters | — | — | 50.0 | — | — | — | — | 99.0 | 1.8 | 100.8 | 100.8 | — |
| Fatty Alcohols | — | — | — | — | — | — | — | — | 9.7 | 9.7 | 9.8 | — |
| Alkanes | — | — | — | — | — | — | — | — | — | — | 0.1 | — |
| Wax Esters | — | — | — | — | — | — | — | — | — | — | — | — |
| Unknown(s) | — | — | — | — | 2.0* | — | — | 0.5 | — | 0.5 | 0.5 | — |
| Heavies | — | — | — | — | — | — | — | — | — | — | — | — |
| Temp. (°C.) | 60 | 40 | 110 | 115 | 110 | 64 | 110 | 112 | 60 | 107 | 205 | 60 |
| Pressure (Bar) | 6.5 | 5.5 | 4.5 | 2.5 | 1.3 | 2.0 | 1.3 | 2.5 | 2.5 | 41.4 | 41.0 | 43.0 |

| Component | Line No. | | | | | | | | | | | |
|---|---|---|---|---|---|---|---|---|---|---|---|---|
| | 119 | 129 | 142 | 150 | 163 | 171 | 176 | 180 | 182 | 186 | 202 | 41 |
| Hydrogen | 48729.5 | 12.0 | — | — | — | — | — | — | — | — | — | — |

TABLE 1-continued

| | | | | | | | | | | | | |
|---|---|---|---|---|---|---|---|---|---|---|---|---|
| Methane | 7.4 | 0.2 | — | — | — | — | — | — | — | — | — | — |
| Methanol | 976.8 | 125.8 | — | trace | trace | — | — | 80 | 78.2 | 0.3 | — | 9.2 |
| Water | 23.5 | 2.6 | — | — | — | — | — | — | — | — | — | — |
| Fatty Acids | — | — | — | — | — | — | — | — | — | — | — | — |
| Methyl Esters | — | 2.0 | 2.0 | — | — | trace | — | — | 1.8 | 1.8 | trace | — |
| Fatty Alcohols | 0.1 | 107.0 | 107.0 | 105.0 | 0.2 | 96.6 | 8.0 | — | 9.8 | 9.8 | 0.1 | — |
| Alkanes | 0.1 | 2.0 | 2.0 | 2.0 | 1.0 | 1.0 | — | — | — | — | — | — |
| Wax Esters | — | — | — | 2.0 | — | — | 2.0 | — | 0.2 | 0.2 | 0.2 | — |
| Unknown(s) | — | 0.5 | 0.5 | 0.5 | — | 0.5 | — | — | — | — | — | — |
| Heavies | — | — | — | — | — | — | 0.2 | — | 0.2 | 0.2 | 0.2 | — |
| Temp. (°C.) | 60 | 60 | 240 | 180 | 60 | 60 | 240 | 64 | 180 | 180 | 60 | 30 |
| Pressure (Bar) | 39.7 | 39.7 | 1.5 | 1.5 | 2.0 | 2.0 | 0.013 | 44 | 41.3 | 1.3 | 2.0 | 2.5 |

Note: * = "unknown(s)" includes dimethyl ether

The plant of FIG. 1 can be modified to operate using an alkali metal alkoxide as the transesterification catalyst in place of an alkyl titanate. In this case the temperature of the crude fatty alcohol stream in line 144 is adjusted to 45° C. in heat exchanger 145. A solution containing 10% w/v of sodium methoxide in dry methanol is added in line 147 so as to provide a concentration of 0.05% w/v of sodium methoxide in the material flowing in line 148. In this modified form of plant first ester interchange reactor 149 is designed to provide, typically, a residence time therein of about 30 minutes. The material exiting reactor 149 in line 150 is then passed through a bed of ion exchange resin in vessel (not shown) provided in line 150 to neutralise the catalyst. The ion exchange resin of this bed can contain sulphonic acid and/or carboxylic acid groups. The catalyst free stream passes on in line 150 to product column 151.

Removal of the sodium methoxide catalyst prior to distillation in product column 151 is desirable so as to obviate the formation of condensation by-products and dark coloured organic tars, which would be promoted by the presence of sodium methoxide in the mixture at the elevated temperatures prevailing in the product column 151.

Recovery of product alcohol in product column 151 is effected in the same way as for the plant of FIG. 1. The bottom product in lines 172, 176 and 178 is then cooled to about 50° C. in heat exchanger 179. A similar stoichiometric excess of methanol is added from line 180 to the liquid stream from heat exchanger 179 in the form of a solution of sodium methoxide in methanol so as to provide a concentration of about 0.05% w/v sodium methoxide in the mixed stream before entry to second ester interchange reactor 181 which is designed for a residence time of about 120 minutes. The interchanged product stream in line 182 is then passed through a second bed of ion exchange resin (not shown) in line 182. This resin contains, for example, sulphonic acid groups and/or carboxylic acid groups. The resin removes sodium ions from the liquid phase and neutralises the sodium methoxide transesterification catalyst. The neutralised liquid phase passes on in line 182 and 184 to flash column 185.

As the material in line 184 contains no transesterification catalyst there is no need to recycle "heavies" via line 203 (as in the plant of FIG. 1). Moreover, as there is no catalyst remaining in the material in line 184, the risk of reversion of methyl esters to wax esters and loss of methanol vapour in columns 185 and 189 by ester interchange with fatty alcohols product is obviated.

In a still further modification of this plant columns 185 and 189 are replaced by a batch still (not shown). In this case the neutralised material in line 184 is collected until there is sufficient to justify operating the batch still.

FIG. 4 illustrates a further design of esterification tray 15 suitable for use in a laboratory scale reactor 14 or in a commercial scale reactor 14. This comprises a generally frusto-conical partition or diaphragm 250 which extends within wall 251 of reactor 14. The slope of the upper surface of diaphragm 250 is greater than the angle of repose of the solid particulate catalyst. A vapour upcomer 252 is fitted with a cap 253 with a dependent skirt of mesh 254. Downcomer 255 is fitted with a mesh cap 256 and with a seal bucket 257. The upper end of downcomer 255 is positioned so as to provide a suitable retention volume for liquid on tray 15 whilst mesh skirt 254 and mesh cap 256 retain the charge of resin particles on diaphragm 250. Methanol vapour flows up upcomer 252 as indicated by arrow 257, through the space between upcomer 252 and cap 253 as indicated by arrows 258, and through skirt 254 as indicated by arrows 259, and carries with it water vapour resulting from water of esterification formed on a lower tray or trays.

Figure 5B:
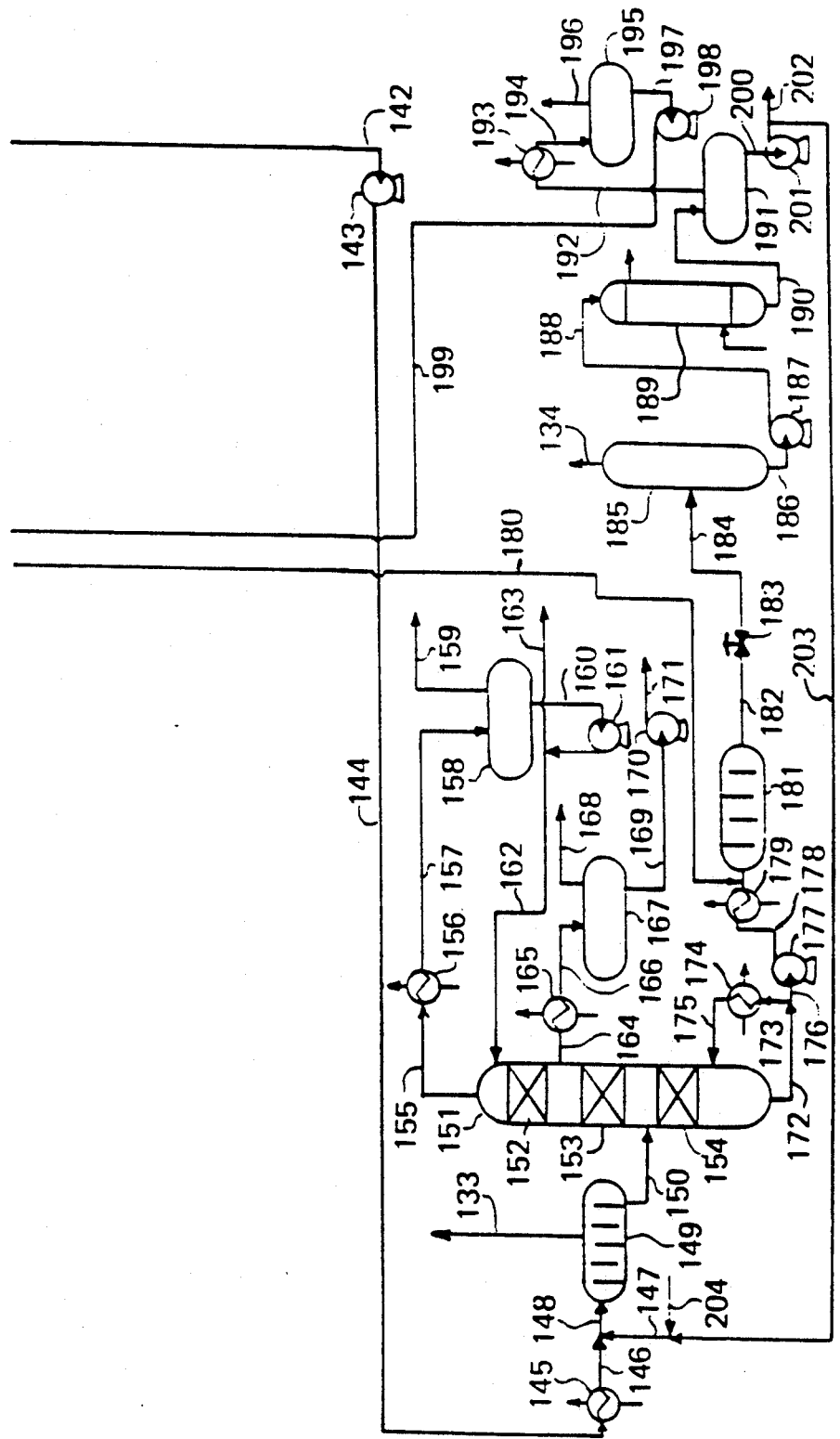

The plant of FIG. 5 is generally similar to that of FIG. 1 and like reference numerals have been used in both Figures to indicate like parts The feed acid in line 1 is typically an unsaturated fatty acid, such as oleic acid.

As the number of theoretical stages in column 14 does not necessarily correspond to the number of trays 15 fitted in column 14, and the number of such theoretical stages may vary, for a particular column, for different feed acids supplied in line 4, the acid content of the methyl ester product in line 23 may vary if the nature of the feed acid in line 4 is changed.

As already mentioned a by-product of ester formation in the column is often a dialkyl ether. The yield of such dialkyl ether by-product is found to be dependent upon the temperature of operation of the reactor 14. Hence by minimising the temperature of operation of column reactor 14 the yield of by-product ether can be minimised. However, a corollary of this is that a lower conversion of acid to ester is obtained at lower operating temperatures. In this case it is possible to optimise the conversion to ester by admixing the ester-containing product, which contains perhaps about 97 mole % to about 99 mole % of ester with the balance being acidic materials, with further alkanol (e.g. methanol) and passing the resulting mixture containing, for example, a 2:1 to 4:1, e.g. 3:1, alkanol:ester molar mixture through a polishing reactor having a fixed bed of a solid esterification catalyst, such as Amberlyst 13, which can be operated at a lower temperature than the column reactor. In this way extremely high overall conversion to ester can be achieved. Such a modified form of plant is illustrated in FIG. 5.

In the plant of FIG. 5 there are six esterification trays 15 and the methyl ester product in line 25 still contains a minor amount of oleic acid. Typically the methyl oleate:oleic acid molar ratio is in the region of 97:3. This mixture is admixed with further methanol supplied from line 301 to form a mixture having a molar ratio of methanol:methyl oleate oleic acid of 3:0.97:0.03. This mixture is supplied in line 302 at a temperature of 60° C. and at a liquid hourly space velocity of 1 hr$^{-1}$ to a further esterification reactor 303 containing a fixed bed 304 of an acid:c ion exchange resin, such as Amberlyst 13. The resulting mixture flows on in line 305 to a further distillation column 306. Methanol vapour passes overhead via line 307 to column 29 via line 26. Liquid methanol to form reflux streams for columns 29 and 306 and the stream in line 301 is pumped from condensate drum 32 via line 34 by pump 35 through lines 36 and 308. The methanol to form the reflux streams flows on in line 309 via line 37 to column 29 and via line 310 to column 306. The bottom product from column 306 in line 311 comprises essentially pure methyl oleate (of purity at least 99.5 mole %). Part is recycled to column 306 by way of line 312 via column reboiler 313 and line 314, whilst the remainder is passed to vaporiser 100 in line 315.

Part of a modified form of plant is illustrated in FIG. 6. This is similar to the plant of FIG. 5 except for the hydrogenation section. Like reference numerals indicate like parts in FIGS. 5 and 6.

The plant of FIG. 6 is designed for use with a variety of different fatty acid feedstocks. Hence the ester (or the main constituent of an ester mixture) supplied in line 315 to vaporiser 100 may at one time be, for example, methyl laurate, whilst at another time it is methyl stearate. To ensure that the feed mixture in line 109 to the hydrogenation reactor 110 is in the vapour phase a higher H$_2$:ester molar ratio must be used when the ester used is, for example, methyl stearate than when it is methyl laurate, due to the lower volatility of the higher molecular weight ester. In addition it will usually be expedient to adjust the heat input to heat exchanger 127 so as to increase the temperature of the hydrogen supplied in line 128 and hence cause an increase in the temperature of the feed mixture in line 109. The increased inlet temperature to hydrogenation reactor 110 contributes to increased rates of reaction within the catalyst charge 111 with the result that hydrogenation is achieved within a smaller volume of catalyst at the inlet end of the catalyst charge 111 than is the case when methyl laurate is the ester or the main component of the ester mixture. Hence the outlet end of the catalyst charge 111 is not serving any useful function in this case. As reactor 110 is operated adiabatically, the result is that the vaporous reaction mixture is spending an appreciable time at outlet temperature in contact with the catalyst. This situation is disadvantageous since it may lead to increased by-product formation, e.g. to formation of additional minor amounts of alkanes. To avoid this situation hydrogenation reactor 110 is provided in the plant of FIG. 6 with three alternative outlet ports 320, 321 and 322, in addition to line 112 These outlet ports 320, 321, and 322 are connected to an outlet manifold 323. A bypass line 324 allows a supplementary flow of hydrogen containing gas to be introduced into the bottom of hydrogenation reactor 110 when one of the outlets, 320, 321 or 322 is in use. This supplementary flow of hydrogen prevents condensation of any liquid on the lower part of the catalyst charge. The catalyst charge 111 itself can be split into several discreet beds with each supplementary outlet 320, 321 and 322 being connected between a respective pair of beds. Alternatively the catalyst charge can be a unitary charge with collector devices, each connected to a respective one of the outlets 320, 321 and 322, buried in the catalyst charge. Hence in this case there are not separate beds of catalyst in the sense of having separate discreet charges of catalyst arranged in series but rather the beds comprise separate sections of a unitary catalyst charge.

Besides allowing the plant operator to minimise by-product formation when utilising high boiling fatty acid feedstocks the provision of supplementary outlets 320, 321 and 322 also permit account to be taken of any loss of catalyst activity with time due to ageing of the catalyst charge.

Variants in design of the hydrogenation reactor 110 are illustrated in FIGS. 7 and 8. FIGS. 9 and 10 show details of a form of distributor/collector for one of the supplementary ports fitted to the reactor 110 shown in FIGS. 6 to 8.

In the modified design of FIG. 7 it is the point of inlet of the vaporous mixture to hydrogenation reactor 110 that can be varied, rather than the point of outlet. In this case reactor 110 has a number of supplementary inlets 325, 326 and 327, connected to an inlet manifold 328, and flow to reactor 110 is controlled by valves 329, 330, 331 and 332. Also hydrogen bypass line 324 is connected in this design to line 315, flow through line 324 being controlled by valve 333. Reference numerals 334 indicate diagrammatically distributors within catalyst charge 111 each connected to a respective inlet 325, 326 or 327.

FIG. 8 illustrates a further modified design of hydrogenation reactor 110 in which discrete individual sections of the catalyst charge 111 can be used in sequence to suit the desired reaction kinetics and equilibria within an acceptable range of reaction and vaporisation temperatures. This has a number of supplementary lines 335, 336, 337 and 338 connected to a line 339 which connects lines 315 and 312. Line 340 connects lines 336 and 338. Supplementary hydrogen can be fed to the reactor 110 by either of lines 341 and 342. Valves 343 to 352 can be used to control flow through reactor 110. A typical operating sequence might be as set out in Table 2.

TABLE 2

| | Valve No. | | | | | | | | | |
|---|---|---|---|---|---|---|---|---|---|---|
| Phase No. | 343 | 344 | 345 | 346 | 347 | 348 | 349 | 350 | 351 | 352 |
| 1 | O | X | X | X | X | O | X | X | O | X |
| 2 | X | O | X | O | X | X | X | O | O | X |
| 3 | X | O | X | X | O | X | X | X | X | O |
| 4 | X | O | X | O | X | X | X | X | X | O |
| 5 | X | O | O | X | X | X | X | X | X | O |

TABLE 2-continued

| Phase No. | Valve No. | | | | | | | | | |
|---|---|---|---|---|---|---|---|---|---|---|
| | 343 | 344 | 345 | 346 | 347 | 348 | 349 | 350 | 351 | 352 |
| 6 | O | X | X | X | X | X | X | X | X | O |

Note: In Table 2 "O" indicates an open valve and "X" indicates a closed valve.

FIGS. 9 and 10 show one form of distributor or collector 334 in part of a hydrogenation reactor 110. This takes the form of a lozenge ring covered with fine mesh to prevent entry of catalyst particles. As can be seen from FIG. 9 each distributor/collector is immersed in the catalyst charge 111.

The invention is further illustrated in the following Examples.

EXAMPLES 1

A crude fatty alcohol product containing a minor amount of unconverted fatty acid methyl esters was prepared by hydrogenating in a laboratory hydrogenation reactor under vapour phase conditions (i.e. under conditions such that the reaction mixture in contact with the catalyst was at all times above its dew point) a mixture of fatty acid methyl esters obtained from a "topped and tailed" fatty acid mixture produced by hydrolysis of coconut oil. The catalyst used was a reduced copper oxide-zinc oxide ester hydrogenation catalyst. Prior to use the crude alcohol product mixture was distilled to remove substantially all the methanol produced as coproduct in the hydrogenation step.

Three samples of the substantially methanol free crude fatty alcohol product were each heated to 200° C. under a nitrogen atmosphere for 30 minutes at 0.99 bar with 0.03% w/w of Tilcom BIP (trade mark of Tioxide Chemical Division of British Titan Products p.l.c.). This material is reported to be a mixed iso-propyl/n-butyl titanate. Subsequent analysis showed that, in the presence of a large excess of fatty alcohols and under conditions allowing methanol to escape from the reaction system, substantially all of the methyl esters had been transformed into wax esters. The results are plotted in Table 3 below which indicates the amounts of the components present in % w/w. In Table 3 "$C_{12}$ Me ester" means methyl dodecanoate, whilst "$C_{14}$ Me ester", "$C_{16}$ Me ester", and "$C_{18}$ Me ester" represent respectively the corresponding methyl esters of the $C_{14}$, $C_{16}$ and $C_{18}$ carboxylic acids. There were detected sixteen unidentified compounds, listed as "Unknowns 1 to 16" in Table 3, in minor or trace amounts.

TABLE 3

| COMPONENT | FEED | PRODUCT | | |
|---|---|---|---|---|
| | | Run 1 | Run 2 | Run 3 |
| Methanol | 2.19 | 0.03 | 0.11 | 0.02 |
| $C_{12}$ Alkane | 0.34 | 0.27 | 0.20 | 0.24 |
| $C_{14}$ Alkane | 0.37 | 0.37 | 0.34 | 0.34 |
| $C_{16}$ Alkane | 0.31 | 0.35 | 0.33 | 0.33 |
| Unknown Compounds | | | | |
| 1 to 6 | 1.34 | 1.68 | 1.75 | 1.90 |
| ($C_{12}$ Me Ester + $C_{18}$ Alkane) | 1.79* | 0.06 | 0.10 | 0.04 |
| Unknowns 7 + 8 | 0.16 | 0.3 | 0.49 | 0.33 |
| Unknowns 9 + 10 | 0.87 | trace | trace | trace |
| $C_{12}$ Alcohol | 57.30 | 56.97 | 55.86 | 54.33 |
| $C_{14}$ Me Ester | 0.21 | trace | trace | trace |
| Unknowns 11 to 13 | 0.17 | 0.17 | 0.14 | 0.23 |
| $C_{14}$ Alcohol | 24.64 | 24.86 | 24.94 | 26.52 |
| $C_{16}$ Me Ester | 0.09 | trace | trace | trace |
| Unknowns 14 + 15 | 0.14 | 0.03 | 0.03 | 0.08 |
| $C_{16}$ Alcohol | 9.45 | 9.42 | 9.66 | 9.47 |
| $C_{18}$ Me Ester | 0.23 | 0.02 | 0.03 | 0.03 |

TABLE 3-continued

| COMPONENT | FEED | PRODUCT | | |
|---|---|---|---|---|
| | | Run 1 | Run 2 | Run 3 |
| Unknown 16 | 0.05 | trace | trace | trace |
| $C_{18}$ Alcohol | 0.35 | 0.45 | 0.50 | 0.46 |
| Wax Esters: | | | | |
| (a) $C_{12}$—$C_{12}$ | — | 2.78 | 2.60 | 3.20 |
| (b) $C_{12}$—$C_{14}$ | — | 1.42 | 1.72 | 1.68 |
| (c) $C_{12}$—$C_{16}$ | — | 0.75 | 0.80 | 0.67 |
| (d) $C_{14}$—$C_{14}$ | — | trace | trace | 0.08 |

*Components not resolved.

In Table 3 the wax esters are identified variously as (a) $C_{12}$-$C_{12}$, (b) $C_{12}$-$C_{14}$, (c) $C_{12}$-$C_{16}$ and (d) $C_{14}$-$C_{14}$. These materials are thought, by reason of their gas chromatographic retention times, to represent respectively:

(a) the ester of a $C_{12}$ alkanol with a $C_{12}$ fatty acid;
(b) mixture of esters of a $C_{12}$ alkanol with a $C_{14}$ fatty acid and of a $C_{14}$ alkanol with a $C_{12}$ fatty acid;
(c) mixture of esters of a $C_{12}$ alkanol with a $C_{16}$ fatty acid and of a $C_{16}$ alkanol with a $C_{12}$ fatty acid; and
(d) the ester of a $C_{14}$ alkanol with a $C_{14}$ fatty acid.

The results plotted in Table 3 were obtained using a Pye Unicam 4500 Gas Chromatograph fitted with 25 metre long Nordian NB351 FAME capillary column and with a flame ionisation detector. The carrier gas was helium at a column inlet pressure of 2.39 bar. The sample injection volume was 0.4 microlitres. The column was temperature programmed as as follows: 2 minutes at 80° C. after sample injection, followed by heating at 8° C. per minute to 230° C., whereafter the temperature was maintained at this value. The injection port temperature was 250° C. and the detector temperature was 270° C. A sample stream split ratio of 40 to 50:1 was used. It is clear from these results that, under the influence of the transesterification catalyst, the methyl esters of the $C_{12}$, $C_{14}$, $C_{16}$ and $C_{18}$ fatty acids are smoothly converted to wax esters. It should be noted, however, that the gas chromatographic technique employed, although resolving the wax esters in total carbon number order, did not enable good resolution between wax esters containing the same number of carbon atoms. For example, the resolution achieved between a $C_{12}$-$C_{16}$ wax ester and a $C_{14}$-$C_{14}$ wax ester was relatively poor.

EXAMPLE 2

665 grams of crude fatty alcohol product which had been subjected to transesterification under the conditions outlined in Example 1 were distilled under vacuum in a simple laboratory distillation unit, the boiler of which was fitted with a short packed column to prevent droplet entrainment. The dimensions of the packed column were 2.5 cm diameter ×30 cm high, packed with 4 mm Raschig rings. The results are summarised in Tables 4 and 5 below. The analysis figures of Table 5 are again expressed as % w/w. The abbreviations used in Table 5 are the same as those used in Table 3.

TABLE 4

| Fraction | Fore run | Product | Residue |
|---|---|---|---|
| Pressure (bar) | 0.014 | 0.013 | 0.013 |
| Temperature distilled | up to 141° C. | 141-170° C. | Not |
| Weight (g) | 96.1 | 537.1 | 30.0 |

TABLE 5
ANALYSIS

| Fraction | Fore run | Product | Residue |
|---|---|---|---|
| Methanol | trace | — | — |
| Unknown 1 | 0.84 | — | — |
| $C_{12}$ Alkane | 1.22 | 0.04 | — |
| Unknown 2 | 1.53 | — | — |
| $C_{14}$ Alkane | 1.35 | 0.21 | — |
| Unknown 3 | 0.91 | — | — |
| Unknown 4 | 0.17 | — | — |
| $C_{16}$ Alkane | 0.47 | 0.33 | — |
| Unknown 5 | 2.36 | — | — |
| Unknown 6 | 0.46 | — | — |
| $C_{12}$ Me Ester + $C_{18}$ Alkane | 0.03 | 0.01 | 0.01 |
| Unknown 7-10 | 0.60 | 0.40 | 0.04 |
| $C_{12}$ Alcohol | 75.34 | 59.66 | 0.30 |
| $C_{14}$ Me Ester | trace | — | — |
| Unknown 11-12 | 0.11 | 0.2 | — |
| $C_{14}$ Alcohol | 10.24 | 29.51 | 1.50 |
| $C_{16}$ Me Ester | 0.03 | — | — |
| Unknown 13 | trace | trace | trace |
| Unknown 14-15 | 0.01 | — | — |
| $C_{16}$ Alcohol | 3.16 | 8.91 | 6.86 |
| $C_{18}$ Me Ester | 0.09 | — | — |
| $C_{18}$ Alcohol | 0.29 | 0.06 | 0.88 |
| Wax esters: | | | |
| $C_{12}$—$C_{12}$ | 0.02 | — | 0.37 |
| Other wax esters | 0.28 | 0.8 | 81.66 |
| Other unknowns | 0.09 | — | 8.36 |

Because the transesterification catalyst remained active throughout the distillation and because the lower alcohols were progressively removed from the system by the distillation procedure, the wax esters remaining in the distillation residue were of higher molecular weight than in the starting material. In other words there was continuous ester interchange amongst the wax esters during distillation with a progressive loss of the more volatile fatty alcohol components to the distillate.

EXAMPLE 3

The distillation residue of Tables 4 and 5 was divided into two portions. One portion was heated to 180° C. for 2 hours with methanol at a methanol:wax ester mole ratio of 20:1 and the other portion was heated at the same temperature and for the same time but at a methanol:wax ester ratio of 40:1. Upon quench cooling analyses in % w/w were obtained, using the gas chromatographic technique of Example 2, as set out in Table 6 below. The abbreviations in Table 6 are the same as are used in Tables 3 and 5. The analytical figures are expressed on a methanol free basis.

TABLE 6

| | Portion No. 1 | Portion No. 2 |
|---|---|---|
| $C_{12}$ Me ester | 32.94 | 34.56 |
| $C_{12}$ Alcohol | 0.17 | 0.13 |
| $C_{14}$ Me ester | 4.48 | 4.88 |
| $C_{14}$ Alcohol | 2.54 | 2.43 |
| $C_{16}$ Me ester | 0.56 | 0.62 |
| $C_{16}$ Alcohol | 41.27 | 42.75 |
| $C_{18}$ Me ester | 0.33 | trace |

TABLE 6-continued

| | Portion No. 1 | Portion No. 2 |
|---|---|---|
| $C_{18}$ Alcohol | 7.85 | 8.16 |
| Wax esters | | |
| (a) $C_{12}$—$C_{12}$ | 0.02 | trace |
| (b) $C_{12}$—$C_{14}$ | 0.27 | 0.33 |
| (c) $C_{12}$—$C_{16}$ | 7.04 | 5.17 |
| (d) $C_{14}$—$C_{14}$ | 2.52 | 0.98 |

It can be seen from these results that, in comparison with the composition of the residue of Table 5, treatment with methanol has effected a considerable conversion of the wax esters to $C_{12}$, $C_{14}$, $C_{16}$ and $C_{18}$ fatty alcohols and to the methyl esters of $C_{12}$, $C_{14}$, $C_{16}$ and $C_{18}$ fatty acids. This conversion has, moreover, been effected without the addition of further alkyl titanate transesterification catalyst, thus demonstrating that the transesterification catalytic activity has survived the vacuum distillation step of Example 2.

EXAMPLE 4

A laboratory scale column reactor with an internal diameter of 76.2 mm made of glass QVF components and having ten trays one above another was used. Each tray had the form illustrated in FIG. 5. The column reactor was lagged and wound with external electrical heating tapes. Each tray had its own temperature control system. The top tray contained no resin and acted as a liquid scrubbing tray to limit losses of the acid feed or of the ester product. The second tray from the top also contained no resin and was supplied with the acid feed. The remaining eight trays each held a charge of Amberlyst 16 ion exchange resin which had been sieved to remove beads with a particle size less than 355 μm and then washed extensively with methanol and dried at 105° C. to constant weight. The mesh size of the stainless steel mesh of skirt 254 and of cap 256 was 300 μm. Dry methanol was vaporised by passage through a coil immersed in an oil bath at 150° C. and the resulting vapour was fed to the bottom of the column reactor below the lowermost tray. Ech tray held about 240 ml of liquid. The resin charge on each tray corresponded to 14% by weight calculated as dry resin based on the liquid charge on each tray. The overhead vapour from the column reactor, which consisted of unreacted methanol, water which is produced in the course of esterification, and a minor amount of by-product dimethyl ether, was condensed. A constant head overflow device was used to control the rate of removal of product esters from the column reactor.

At start up the column reactor was charged with resin and with methyl laurate. When the methanol flow and the temperatures of the various trays had stabilised a feed of 50 mole % methyl laurate, 40 mole % lauric acid, and 10 mole % myristic acid was supplied to the column. This feed mixture was similar to the mixture in line 20 of FIG. 1 when that plant is supplied in line 4 with a mixture of lauric acid and myristic acid. The level of $C_{14}$ ester in the bottoms product from the column reactor was monitored until an equilibrium level was attained. The liquid on each tray was analysed. The results are summarised in Table 7 below; the trays are numbered from 1 to 10, tray No. 1 being the top tray and tray No. 10 being the bottom tray.

TABLE 7

| MeOH:Acid mole ratio | 5:1 | 3.6:1 | 3:1 |
|---|---|---|---|
| Residence time (hours) | 2.6 | 2.2 | 2.0 |
| Tray No. | Mole % Conversion | | |
| 5 | 98.32 | 96.53 | 95.16 |
| 6 | 99.39 | 98.76 | 97.05 |
| 7 | 99.62 | 99.15 | 97.25 |
| 8 | 99.87 | 99.45 | 98.74 |
| 9 | 99.93 | 99.75 | 99.48 |
| 10 | ND | 99.81 | 99.76 |
| DME make | 3.0 | 2.7 | 1.5 |

In Table 7 and in the following Tables "N.D." means "not determined", whilst "DME" means "dimethyl ether", the "DME make" being expressed as percentage by weight of the acid feed.

EXAMPLE 5

The same column reactor as was used in Example 4 was fed with a mixture of natural straight chain fatty acids of the following composition:

| Component | % by weight |
|---|---|
| $C_8$ acid | 5.10 |
| $C_{10}$ acid | 4.62 |
| $C_{12}$ acid | 40.64 |
| $C_{14}$ acid | 14.12 |
| $C_{16}$ acid | 9.57 |
| $C_{18}$ acids | 25.01 |
| Unknowns | 0.77 |
| $H_2O$ | 0.17 |

The results are summarised in Table 8.

TABLE 8

| MeOH:Acid mole ratio | 2.7:1 | 3.8:1 | 4.2:1 | 4.1:1 | 4.7:1 | 6.7:1 |
|---|---|---|---|---|---|---|
| Residence Time (hours) | 1.9 | 3.3 | 3.6 | 3.5 | 4.6 | 4.7 |
| Tray No | Mole % Conversion | | | | | |
| 5 | 61.22 | 66.54 | 68.89 | 68.01 | 69.02 | 79.82 |
| 6 | ND | ND | ND | ND | ND | ND |
| 7 | 86.20 | 89.74 | 91.78 | 90.16 | 91.78 | 92.38 |
| 8 | 92.50 | 94.62 | 96.14 | 95.29 | 96.22 | 98.07 |
| 9 | 95.28 | 97.46 | 98.15 | 97.68 | 98.11 | 99.20 |
| 10 | 97.53 | 98.77 | 99.12 | 98.90 | 99.30 | 99.64 |
| DME Make | 2.0 | 2.8 | 2.5 | 2.7 | 2.7 | 2.8 |
| Average Temperature (°C.) | 112 | 107 | 104 | 111 | 112 | 113 |

EXAMPLE 6

The procedure of Example 5 was repeated using a 51.6:48.4 acid:ester mole ratio feed mixture. Such a mixture corresponded to a typical feed mixture in line 20 of FIG. 5. The acids used were a mixture of natural straight chain fatty acids comprising 65% by weight $C_{12}$ acid, 25% by weight $C_{14}$ acid, and 10% by weight $C_{16}$ acid. The results are shown in Table 9 below. In this Example the amounts of resin on a dry basis on each tray corresponded to 10% by weight based upon the liquid retained for each of trays Nos. 3 to 7 and to 5% by weight on the same basis for trays Nos. 8 to 10.

TABLE 9

| MeOH:Acid mole ratio | 3:1 | 2:1 |
|---|---|---|
| Residence time (hours) | 2.5 | 2.5 |
| Tray No | Mole % Conversion | |
| 3 | 70.08 | 67.10 |
| 4 | 83.10 | 79.21 |
| 5 | 91.59 | 88.48 |
| 6 | 96.4 | 94.46 |
| 7 | 98.55 | 97.39 |
| 8 | 99.13 | 98.24 |
| 9 | 99.49 | 98.87 |
| 10 | 99.68 | 99.27 |
| DME Make | 2.1 | 1.3 |
| Average Temperature (°C.) | 110 | 107 |

EXAMPLE 7

Using the column reactor of Example 4 the following esterification reactions between the specified acid and the corresponding alcohol component are carried out with similarly good results with the more volatile reactant in each case being supplied to the bottom of the reactor in vapour form and the less volatile component being supplied in liquid form to the second tray of the reactor:

(a) stearic acid with methanol to methyl stearate;
(b) palmitic acid with ethanol to ethyl palmitate;
(c) arachidic acid with methanol to methyl arachidate.
(d) oleic acid and iso-propanol to yield iso-propyl oleate;
(e) ricinoleic acid and methanol to methyl ricinoleate; and
(f) isostearic acid and methanol to methyl isostearate.

EXAMPLE 8

An ester mixture obtained by esterification of a "topped" coconut fatty acid mixture with methanol was hydrogenated in a laboratory reactor under vapour phase conditions using a reduced copper oxide/zinc oxide catalyst obtained by reduction of PG 88/32 catalyst precursor (obtainable from Davy McKee (London) Limited of Davy House, 68 Hammersmith Road, London, W14 8YW) according to the supplier's instructions. The ester mixture had the following analysis in % by weight: methanol 0.16; $C_{10}$ ester 1.63; $C_{12}$ ester 54.60; $C_{14}$ ester 20.24; $C_{16}$ ester 10.34; $C_{18}$ ester 10.74; $C_{12}$ acid 0.09; $C_{14}$ acid 0.05; $C_{16}$ acid 0.05; $C_{18}$ acid 0.42; "unknowns" 1.61; and $H_2O$ 0.07. The $H_2$:ester molar ratio was 630:1. The results are summarised in Table 10.

TABLE 10

| | Run No. | | | | |
|---|---|---|---|---|---|
| | 1 | 2 | 3 | 4 | 5 |
| Reactor Temp. (°C.) | 215 | 215 | 215 | 215 | 215 |
| LHSV ($hr^{-1}$) | 0.22 | 0.25 | 0.25 | 0.30 | 0.35 |
| Pressure (bar) | 42.36 | 42.70 | 42.70 | 42.70 | 42.36 |
| Conv. $C_{12}$ | 99.6 | 99.2 | 99.2 | 98.6 | 98.0 |
| Sel. $C_{12}$ | 99.2 | 99.3 | 99.3 | 99.4 | 99.5 |
| Conv. $C_{14}$ | 99.8 | 97.8 | 97.5 | 99.6 | 99.7 |
| Sel. $C_{14}$ | 98.1 | 98.2 | 98.2 | 98.7 | 99.1 |
| Conv. $C_{16}$ | 99.7 | 99.8 | 99.8 | 99.7 | 99.9 |
| Sel. $C_{16}$ | 96.6 | 96.9 | 96.9 | 97.8 | 98.5 |
| Conv. $C_{18}$ | 99.9 | 99.3 | 99.3 | 99.7 | 99.8 |
| Sel. $C_{18}$ | 91.9 | 92.6 | 92.6 | 94.5 | 95.4 |

EXAMPLE 9

Following the teachings of Example 8 each of the esters prepared according to Example 7 above is hydrogenated according to the general procedure described in Example 8 and then the hydrogenation product is subjected to transesterification by the procedure of Example 1, followed by distillation as described in Example 2, and then the distillation residue is submitted to a second transesterification step as taught by Example 3. Similarly good results are obtained.

We claim:

1. A process for the production of fatty alcohols in which a fatty acid or fatty acid mixture is esterified in an esterification step with a lower alkanol to form the corresponding lower alkyl fatty acid ester or esters, in which the resulting lower alkyl fatty acid ester or esters is or are subjected to hydrogenation in the presence of a heterogeneous ester hydrogenation catalyst to yield an ester hydrogenation product comprising a fatty alcohol or alcohols, and in which the ester hydrogenation product is subjected to product refining for recovery of fatty alcohol or alcohols therefrom, characterized in that the esterification step includes continuously supplying the fatty acid or fatty acid mixture in liquid phase to an esterification zone maintained under esterification conditions and containing a charge of a solid esterification catalyst containing sulphonic acid groups and/or carboxylic acid groups in countercurrent to a vaporous stream containing vapour of the fatty alkanol, that the esterification zone is supplied with a feed stream of lower alkanol vapour having a water content of less than about 5 mole %, that a vaporous exist stream containing lower alkanol vapour and water of esterification is recovered from the esterification zone, that a lower alkyl fatty acid ester stream is recovered from the esterification zone that contains at least about 99 mole % of lower alkyl fatty acid ester, that lower alkyl fatty acid ester or ester mixture recovered from the esterification step is vaporised in a stream of hydrogen and passed in vapour form through a hydrogenation zone containing a charge of a solid ester hydrogenation catalyst under vapour phase hydrogenation conditions such that the vaporous mixture in contact with the catalyst is always above its dew point, that the resulting hydrogenation product is collected and contains at least about 0.5 mole % of unreacted lower alkyl fatty acid ester in addition to product fatty alcohol or alcohols, that the hydrogenation product is subjected to transesterification in a first transesterification zone maintained under transesterification conditions, thereby to convert unreacted lower alkyl fatty acid ester in the hydrogenation product by reaction with product fatty alcohol or alcohols into a wax ester or wax esters derived from the product alcohol or product alcohols and from a fatty acid moiety of the lower alkyl fatty ester, that lower alkanol is evaporated from the resulting mixture, and that the now substantially lower alkanol free mixture is further distilled to yield (i) an overhead fraction that contains the product alcohol or alcohols and is substantially free from lower alkyl fatty acid ester and (ii) a distillation residue comprising fatty alcohol or alcohols and wax ester or esters.

2. A process according to claim 1, characterised in that the distillation residue (ii) is subjected to transesterification in the presence of added lower alkanol in a second transesterification zone maintained under transesterification conditions, thereby to reconvert wax ester or esters to lower alkyl fatty acid ester or esters and to fatty alcohol or alcohols, that lower alkanol is evaporated from resulting reaction mixture to yield a liquid residue that is substantially free from lower alkanol and that fatty alcohol or alcohols and lower alkyl fatty acid ester or esters present in this liquid residue are distilled to produce (a) an overhead product containing a mixture of lower alkyl fatty acid ester or esters and fatty alcohol or alcohols and (b) a relatively involatile residue.

3. A process according to claim 2, characterised in that an alkyl titanate is used in the second transesterification zone as transesterification catalyst.

4. A process according to claim 3, characterised in that the liquid residue is distilled without prior separation of the transesterification catalyst therefrom to produce overhead product (a) and relatively involatile residue (b).

5. A process according to claim 4, characterised in that at least a part of the relatively involatile residue (b) is recycled to provide transesterification catalyst for use in the first transesterification zone.

6. A process according to any one of claim 1, characterised in that an alkyl titanate is used in the first transesterification zone as transesterification catalyst.

7. A process according to claim 6, characterised in that the intermediate transesterification product from the first transesterification zone is distilled without prior separation of the transesterification catalyst therefrom to produce the overhead product (i) and the distillation residue (ii).

8. A process according to claim 2, characterised in that an alkali metal alkoxide is used in the second transesterification zone as transesterification catalyst.

9. A process according to claim 8, characterised in that the liquid residue is passed through a bed of an acidic ion exchange resin containing —$SO_3H$ and/or —COOH groups to neutralise the alkali metal hydroxide prior to the distillation step to produce overhead product (a) and relatively involatile residue (b).

10. A process according to claim 2 or claim 8, characterised in that an alkali metal alkoxide is used in the first transesterification zone as transesterification catalyst.

11. A process according to claim 10, characterised in that the intermediate transesterification product mixture from the first transesterification zone is passed through a bed of an acidic ion exchange resin containing —$SO_3H$ and/or —COOH groups to neutralise the alkali metal alkoxide prior to the distillation step to produce the overhead product (i) and the distillation residue (ii).

12. A process according to claim 1, characterised in that the lower alkyl fatty acid ester or esters is or are a methyl fatty acid ester or esters and in which the lower alkanol is methanol.

13. A process according to claim 1, characterised in that the esterification step is conducted in a column reactor provided with a plurality of esterification trays mounted one above another, each adapted to hold a predetermined liquid volume and a charge of solid esterification catalyst thereon, liquid downcomer means associated with each esterification tray adapted to allow liquid phase to pass down the column reactor from that esterification tray but to retain solid esterification catalyst thereon, and vapour upcomer means associated with each esterification tray adapted to allow vapour to enter that esterification tray from below and to agitate the mixture of liquid and solid esterification catalyst on that tray, that the fatty acid or fatty acid mixture is supplied in liquid phase to the uppermost one of said plurality of esterification trays whilst the lower alkanol is supplied in vapour form beneath the lowermost one of said plurality of esterification trays, that vapour comprising said lower alkanol and water of esterification is recovered from an upper part of the column reactor, and that a lower alkyl fatty acid ester or ester mixture is recovered from a lower part of the column reactor.

14. A process according to claims 1, characterised in that the lower alkanol is methanol.

15. A process according to claim 14, characterised in that the water content of the methanol vapour supplied to the column reactor is less than about 1 mole %.

16. A process according to claim 13, characterised in that the column reactor is operated at a temperature of from about 80° C. to about 140° C. and at a vapour inlet pressure of from about 0.1 bar to about 25 bar.

17. A process according to claim 1, characterised in that the esterification step includes admixing the lower alkyl fatty acid ester recovered from the first mentioned esterification zone with additional lower alkanol and passing the resulting mixture through a further esterification containing a fixed bed of a solid esterification catalyst.

* * * * *

UNITED STATES PATENT AND TRADEMARK OFFICE
CERTIFICATE OF CORRECTION

PATENT NO. : 5,157,168

DATED : October 20, 1992

INVENTOR(S) : Martyn Wilmott et al.

It is certified that error appears in the above-identified patent and that said Letters Patent is hereby corrected as shown below:

Column 5, line 13, "abou:" should be --about--.

Column 7, line 20, after "alkanol" insert a period --.--

Column 8, line 10, "catalyst liquid" should be --catalyst:liquid--.

Column 11, line 36, after "catalyst" insert a period --.--.

Column 20, Table 1, the last two entries on the line for "Methane" should be --7.6-- and --0.2--.

Column 22, line 40, after "parts" insert a period --.--.

Column 24, line 4, after "112" insert a period --.--.

Column 28, line 44, "Ech" should be --Each--.

UNITED STATES PATENT AND TRADEMARK OFFICE
CERTIFICATE OF CORRECTION

PATENT NO. : 5,157,168

DATED : October 20, 1992

INVENTOR(S) : Martyn Wilmott et al.

It is certified that error appears in the above-identified patent and that said Letters Patent is hereby corrected as shown below:

Column 32, line 15, delete "any one of".

Signed and Sealed this

Ninth Day of November, 1993

Attest:

BRUCE LEHMAN

*Attesting Officer*  *Commissioner of Patents and Trademarks*